United States Patent
Kapulnik et al.

(10) Patent No.: US 7,060,872 B1
(45) Date of Patent: Jun. 13, 2006

(54) METHOD FOR PRODUCING PLANTS HAVING MODIFIED CANOPY SIZE OR SEEDLESS FRUIT

(75) Inventors: Yoram Kapulnik, Carmey Yosef (IL); Idit Ginzberg, Raanana (IL)

(73) Assignee: The State of Israel-Ministry of Agriculture & Rural Development, Agricultural Research Organization, Beit-Dagan (IL)

( * ) Notice: Subject to any disclaimer, the term of this patent is extended or adjusted under 35 U.S.C. 154(b) by 0 days.

(21) Appl. No.: 09/762,243

(22) PCT Filed: Jul. 30, 1999

(86) PCT No.: PCT/IL99/00420

§ 371 (c)(1),
(2), (4) Date: Feb. 5, 2001

(87) PCT Pub. No.: WO00/07427

PCT Pub. Date: Feb. 17, 2000

(30) Foreign Application Priority Data

Aug. 3, 1998 (IL) ..................................... 125632

(51) Int. Cl.
*C12N 15/82* (2006.01)

(52) U.S. Cl. .................................................... 800/290
(58) Field of Classification Search ................ 800/278, 800/287, 288, 290, 298, 303; 435/468, 419, 435/320.1
See application file for complete search history.

(56) References Cited

U.S. PATENT DOCUMENTS 5,530,191 A * 6/1996 Maliga ........................ 800/274
5,689,041 A * 11/1997 Mariani et al. ............. 800/266
5,767,379 A * 6/1998 Baszczynski et al. .... 800/320.1
5,962,769 A * 10/1999 Albertsen et al. ........... 800/303

FOREIGN PATENT DOCUMENTS

WO     WO96/40949    * 12/1996

OTHER PUBLICATIONS

Gitlin et al, 1990, Biochem. J. 269:527-530.*
Wuytswinkel et al, 1998, Plant J. 17:93-97.*
Watanabe et al, 2001, Physiol. Plant. 112:546-551.*
Koop et al, 1996, Planta 199:193-201.*
Zoubenko et al, 1994, Nuc. Acids Res. 22:38-19-3824.*
Binder et al, 1996, Plant Mol. Biol. 32:303-314.*

* cited by examiner

*Primary Examiner*—Anne Kubelik

(57) ABSTRACT

The inventions are methods of generating a plant having modified canopy size or having seedless fruit by transformation with a construct encoding streptavidin operably linked to a secretion signal peptide capable and selecting plants with degeneration of young leaf and/or shoot tissue or degeneration of embryonic tissue, respectively.

2 Claims, 4 Drawing Sheets
(2 of 4 Drawing Sheet(s) Filed in Color)

Fig. 3a stav

Fig. 3b rRNA

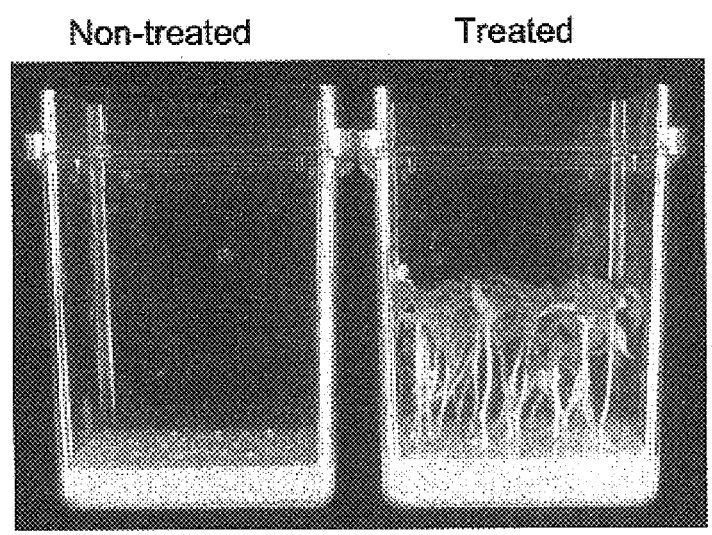
Fig. 6
Fig. 7a  Fig. 7b  Fig. 7c  Fig. 7d
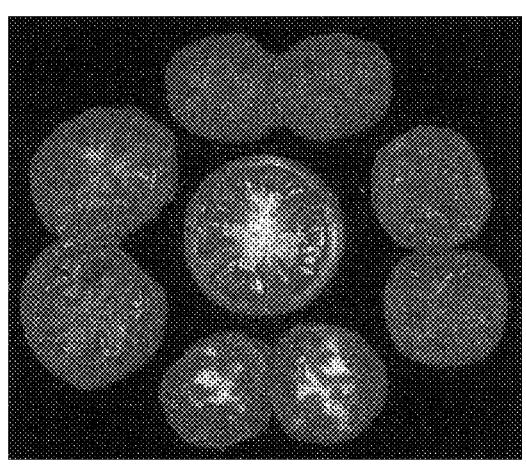
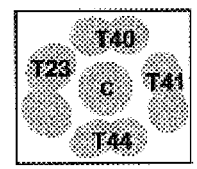
Fig. 8

METHOD FOR PRODUCING PLANTS HAVING MODIFIED CANOPY SIZE OR SEEDLESS FRUIT

FIELD AND BACKGROUND OF THE INVENTION

The present invention relates to a method for effecting selective and optionally reversible cell degeneration in somatic plant tissue. The present invention further relates to plants which display controlled morphological changes as a result of controlled cell degeneration effected while implementing the method and further to nucleic acid expression cassettes for effecting the method.

Ever since the emergence of modem agriculture, cultivated plants have been manipulated in an effort to establish crops with desired traits. Such traits typically include, crop yield and quality, enhanced growth rates and adaptation to various growth conditions.

Various manipulations to crop plants are effected in an effort to produce such desirable traits, the most common of which include exercising optimal growth conditions, pruning, selection of plants with the desired traits and the like. Such manipulations are typically time consuming and tedious to effect, and in addition are also limited in their ability to produce the desirable traits.

As such, more advanced manipulative techniques are often utilized to produce desirable traits in crop plants. Such manipulations include genetic crossing of plants to produce offsprings with favorable traits and directed genetic manipulation of plant genomes, which, with the emergence of recombinant techniques, is rapidly becoming the tool of choice for introducing desirable traits to crop plants.

Such directed genetic manipulation is typically used to confer insect and fungal resistance to plants, to manipulate growth and development, and to manipulate the productivity and quality of the plant derived products.

Since, such manipulation involves the introduction of a specific and specialized gene which is typically effective in a limited variety of plant species, the utilization of such a technique is limited in each case to one or several applicable plant species.

The present invention relates to a method for controlling the morphological development and productivity of crop plants, which method can be applied to a wide variety of plant species. Additional aspects of the present invention will become apparent to those of skills in the art reading the following sections

SUMMARY OF THE INVENTION

According to one aspect of the present invention there is provided a method of effecting degeneration of a somatic plant tissue of a plant, the method comprising the step of expressing in cells of the somatic plant tissue a heterologous protein capable of binding a plant essential factor, wherein the step of expressing the heterologous protein is effected in a fashion, so as to lead to depletion of the essential factor such that plant viability is maintained, while at the same time, degeneration of the somatic plant tissue is effected.

According to another aspect of the present invention there is provided a transgenic plant expressing a heterologous protein capable of binding a plant essential factor, wherein expressing the heterologous protein is effected in a fashion, so as to lead to a depletion of the essential factor such that plant viability is maintained, while at the same time, degeneration of somatic plant tissue of the transgenic plant is effected.

According to yet another aspect of the present invention there is provided a transgenic plant comprising somatic plant cells being transformed with an expression cassette including a first polynucleotide segment under a transcriptional control of a plant promoter, the first polynucleotide segment encoding a heterologous protein which binds a sufficient amount of a plant essential factor to thereby cause degeneration of a somatic plant tissue, while at the same time, maintain plant viability.

According to still another aspect of the present invention there is provided a method for selectively controlling a morphology of a plant, the method comprising the steps of (a) expressing in somatic cells of the plant a heterologous protein capable of binding a plant essential factor, wherein the step of expressing the heterologous protein is effected in a fashion so as to lead to a depletion of the essential factor such that plant viability is maintained, while at the same time, degeneration of the somatic cells is effected; and (b) introducing into a selected portion of the degenerated somatic cells of the plant a neutralizing agent, the neutralizing agent being capable of at least partially reversing the depletion of the plant essential factor, to thereby lead to regeneration of the selective portion of the degenerated somatic cells, so as to selectively control the morphology of the plant.

According to an additional aspect of the present invention there is provided a plant comprising somatic tissue expressing a heterologous protein being bound to a plant essential factor, such that unbound and active form of the plant essential factor is depleted from the somatic plant tissue, thereby effecting degeneration of the somatic plant tissue.

According to yet an additional aspect of the present invention there is provided a nucleic acid expression cassette comprising in a 5' to 3' orientation a first polynucleotide segment including a plant promoter sequence, a second polynucleotide segment coding for a plant leader peptide for directing a protein into a plant cell DNA containing organelle and a third polynucleotide segment, being in frame with the second polynucleotide segment, and coding for a heterologous protein capable of binding a plant essential factor.

According to still an additional aspect of the present invention there is provided a nucleic acid expression cassette comprising in a 5' to 3' orientation a first polynucleotide segment including a plant promoter sequence, a second polynucleotide segment coding for a plant signal peptide for directing a protein into the endoplasmic reticulum and a third polynucleotide segment, being in frame with the second polynucleotide segment, and coding for a heterologous protein capable of binding a plant essential factor.

According to one further aspect of the present invention there is provided a nucleic acid expression cassette comprising in a 5' to 3' orientation a first polynucleotide segment including a plant promoter sequence, a second polynucleotide segment coding for a plant signal peptide, a third polynucleotide segment coding for a bacterial signal peptide and a fourth polynucleotide segment coding for a biotin binding protein, the second, third and fourth polynucleotide segments being in frame.

According to further features in preferred embodiments of the invention described below, the fashion is selected according to at least one criterion selected from the group consisting of (i) a level of expression of the heterologous protein; (ii) a distribution of the heterologous protein in the plant tissue; (iii) binding activity of the heterologous protein toward the plant essential factor; (iv) abundance and distribution of the plant essential factor in the cells; and (v) a level of the factor externally provided to the somatic plant tissue.

According to still further features in the described preferred embodiments the method further comprising the step of introducing into the cells of the degenerated somatic plant tissue a neutralizing agent, the neutralizing agent being capable of reversing the depletion of the plant essential factor to thereby lead to a regeneration of degenerated somatic plant tissue.

According to still further features in the described preferred embodiments the plant essential factor is biotin.

According to still further features in the described preferred embodiments the plant essential factor is selected from the group consisting of an iron ion, thiamin, a calcium ion, and a zinc ion.

According to still further features in the described preferred embodiments the heterologous protein is a biotin binding protein.

According to still further features in the described preferred embodiments the heterologous protein is selected from the group consisting of avidin, streptavidin and biotin binding derivatives and modificants thereof.

According to still further features in the described preferred embodiments the heterologous protein is selected from the group consisting of an iron binding protein, a zinc binding protein, a calcium binding protein and a thiamin binding protein.

According to still further features in the described preferred embodiments the heterologous protein is expressed within the cytoplasm of the cells of the somatic plant tissue so as to lead to the depletion of the essential factor present within the cytoplasm, such that the plant viability is maintained, while at the same time, the degeneration of the somatic plant tissue is effected.

According to still further features in the described preferred embodiments the heterologous protein is expressed within a DNA containing organelle of the cells of the somatic plant tissue so as to lead to the depletion of the essential factor present within the DNA containing organelle, such that the plant viability is maintained, while at the same time, the degeneration of the somatic plant tissue is effected.

According to still further features in the described preferred embodiments the heterologous protein includes a leader peptide capable of self targeting into a DNA containing organelle, such that when the heterologous protein is expressed within the cytoplasm of the cells of the somatic plant tissue the leader peptide directs the heterologous protein into the DNA containing organelle, so as to lead to the depletion of the essential factor present within the DNA containing organelle such that the plant viability is maintained, while at the same time, the degeneration of the somatic plant tissue is effected.

According to still further features in the described preferred embodiments the heterologous protein includes a signal peptide capable of targeting the heterologous protein into the endoplasmic reticulum.

According to still further features in the described preferred embodiments the degeneration of plant somatic tissue is effected for controlling a morphology of the plant.

According to still further features in the described preferred embodiments the degeneration of plant somatic tissue is effected for controlling a development of the plant.

According to still further features in the described preferred embodiments the step of introducing into the cells of the degenerated somatic plant tissue a neutralizing agent, includes selectively expressing within the cells of the somatic plant tissue a neutralizing agent selected from the group consisting of antisense RNA and a ribozyme to thereby prevent the expression of at least a portion of the heterologous protein so as to at least partially reverse the depletion of the plant essential factor and to thereby lead to the regeneration of the degenerated somatic tissue.

According to still further features in the described preferred embodiments the step of introducing into the cells of the degenerated somatic plant tissue a neutralizing agent, includes selectively expressing within the cells of the somatic plant tissue an antagonist protein capable of preventing or interrupting the binding of the heterologous protein with the plant essential factor, so as to at least partially reverse the depletion of the plant essential factor and to thereby lead to regeneration of the degenerated somatic plant tissue.

According to still further features in the described preferred embodiments the neutralizing factor is the plant essential factor and the step of introducing the neutralizing agent into the cells of the degenerated somatic plant tissue includes externally applying the plant essential factor to at least a portion of the degenerated somatic plant tissue, to thereby lead to at least partial regeneration of the degenerated somatic plant tissue.

According to still further features in the described preferred embodiments the promoter is a plant derived promoter and a plant virus derived promoter.

According to still further features in the described preferred embodiments the plant promoter is selected from the group consisting of a constitutive promoter, a tissue specific promoter, a developmentally regulated promoter and an inducible promoter.

The present invention successfully addresses the shortcomings of the presently known configurations by providing new tools for artificially controlling plant development and morphology, which may find uses in, for example, (i) decrease the number of flowers in fruit producing plants so as to increase the number of fruits which reach maturity; (ii) decrease the number of fruits so that each fruit produced is larger; (iii) degenerate seeds so that they are unable to germinate in order to avoid growing of new crops by unauthorized persons in possession of the parent plants; (iv) produce seedless fruits; (v) modify flower shape by altering the biogenesis of the floral tissue; (vi) modify and/or arrest the development of somatic tissue in order to reduce the need for clipping, shearing, trimming, pruning, cutting, etc.; (vii) postpone/delay or eliminate flowering in forage crops to extend the vegetative growth of the plant. (viii) block or reduce successful penetration and colonization of plant pathogens (such as *Orobanche* spp.) by reducing or arresting the viability of invaded cells; (ix) generate dwarfed plants with numerous stems and a bushy phenotype with no growth retardation inflicted upon the individual stems, this is especially applicable under "space limited" growth conditions; (x) use of the degenerating characteristic phenotype as a reporter gene in promoterless trapping cassettes and to localize expression of genes and promoters in plants; (xi) generate flowering plants which do not produce fruit by expressing the essential factor binding protein in the flower's stigma, this is desirable, for example, in ornamental plant cultivation since it considerably prolongs flower shelf-life.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention is herein described, by way of example only, with reference to the accompanying drawings, wherein:

FIG. 6 demonstrates germination of transgenic seeds derived from either a non-biotin treated plant or from the same plant treated externally with biotin. While normal germination was evident for the seeds obtained form the biotin treated plant, the seeds from the non-treated plant failed to germinate under otherwise similar conditions.

FIG. 7 depicts the morphology and development of leaves of 6 weeks old plants obtained from a non transgenic plant (A); a transgenic plant expressing the sps streptavidin cassette and treated daily with biotin (B); a transgenic plant expressing the sps streptavidin construct and treated once (after 3 weeks) with biotin (C); and a transgenic plant expressing the sps streptavidin cassette and not treated with biotin (D).

FIG. 8 depicts tomato seed development in a tomato fruit of a control plant (C) relative to seedless fruits obtained from transgenic plants expressing various streptavidin levels under the control of the Tob promoter, which is known to direct gene expression in early embryonic developmental stages.

DESCRIPTION OF THE PREFERRED EMBODIMENTS

Figure 1:
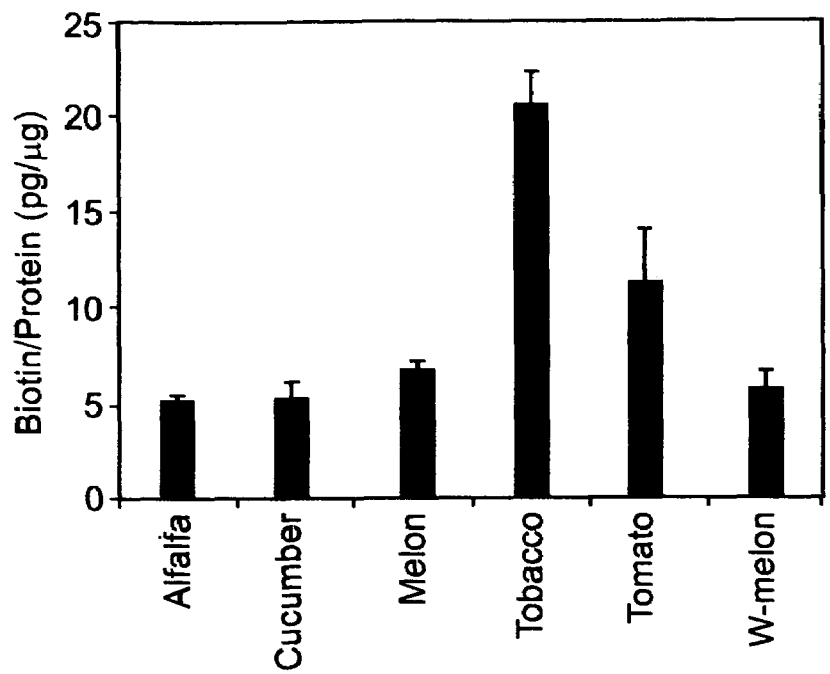
FIG. 1 is a bar-graph depicting the biotin content of several crop plants as determined using a bacterial assay. The assay which is further described in the Examples section that follows, was performed in triplicates and the results were normalized per protein content for each sample.

The present invention is of a method which can be used to effect cell degeneration in somatic plant tissue. The present invention is further of a method which can be used to effect reversible cell degeneration in somatic plant tissue. Specifically, the present invention can be used to control the morphology and development of somatic plant tissue by expressing within cells of somatic tissue a heterologous protein which can effectively bind a plant essential factor such as, for example, biotin.

Biotin is an essential cofactor for a variety of carboxylases and decarboxylases found in diverse metabolic pathways of all organisms. Despite the ubiquitous requirement for biotin, its de novo synthesis is restricted to plants and some microbes. Biotin biosynthesis, from the precursors pimelic acid and alanine, has been best studied in *Escherichia coli*, in which six genes were found to involved. Recent data indicate that biotin may be synthesized by a very similar route in plants. Whereas bacteria use all of their synthesized biotin for biotinylation of biotin-containing proteins, plants accumulate most of their biotin as the protein-free molecule. A study conducted with pea leaves showed the existence of a free biotin pool in the cytosolic compartment, accounting for about 90% of the total (free plus protein-bound) biotin. Thus, it was suggested that biotin biosynthesis occurs in the cytosol.

Avidin, either isolated from egg-white or streptavidin are biotin binding proteins. Streptavidin is a component in the antibiotic complex of *Streptomyces avidinii*, and is similar to avidin. It is a tetrameric protein with binding affinity to biotin of Ka $\sim 10^{-15}$ $M^{-1}$. Unlike avidin, which is a glycosylated, basic protein, streptavidin is a non-glycosylated, neutral protein. The molecular mass of the streptavidin monomer is about 16,000 Da. Similar to avidin, the binding of biotin to streptavidin increases the stability of the molecule. Proteolytic removal of the N- and C-termini of streptavidin, yields core-streptavidin with a molecular mass of 13,200 Da. The interaction of core-streptavidin with biotinylated proteins is significantly improved over that of the intact unprocessed molecule. The resistance of streptavidin and the streptavidin-biotin complexes to denaturing agents is even greater than that of avidin.

The expression of a biotin binding protein in plants has been reported in the scientific and patent literature in two contexts.

The first, as reported by Hood et al., and by Kusnadi et al., uses such expression for commercial production of avidin. The second, described in WO 96/40949 and 99/04023 uses such expression for the reversible induction of male sterility in plants.

Hood et al., reports of production of avidin under the control of a constitutive promoter by use of transgenic maize. The purpose of this transgenic plant, was to produce a commercial amount of avidin from a plant source as an alternative for production of avidin from an animal or bacterial source. The avidin was extracted from the dry seeds of the plant. This study also reports that, as a side affect, the presence of the avidin gene correlate with partial or total male sterility, i.e., non production of viable pollen or of pollen altogether. However, other than the degeneration of pollen cells, the remaining somatic cells of the plants in this publication were not reported to be other than normal, and in fact the plant was able to continuously produce avidin without showing any degeneration of any of its somatic tissue.

Similarly, the study conducted by Kusnadi et al., utilized whole plant expression of avidin for the purposes of subsequent extraction of commercial quantities of the recombinant avidin. This study does not report or suggest the existence of somatic cell degeneration as a result of such expression.

WO 96/40949 and WO 99/04023 teach a method for controlling fertility of plants using DNA molecules that encode avidin. In particular they relate to transgenic plants that express avidin under constitutive, tissue specific or inducible promoters for the purposes of producing male sterile plants. WO 96/40949 and WO 99/04023 fail to describe or discuss the use of such a mechanism for the purposes of somatic cell degeneration.

As is evident from the information disclosed in both the scientific and patent literature mentioned above, constitutive, whole plant, expression of a biotin binding protein was practiced to some extent in the prior art. It will be appreciated that due to the lack of documentation pointing otherwise, such constitutive expression did not yield somatic cell degeneration. In addition, since the studies conducted by Hood et al., and Kusnadi et al., were aimed at producing and harvesting commercial quantities of avidin, somatic cell degeneration would severely decrease the effectiveness of this application and as such would be ineffective.

WO 96/40949 and 99/04023 report of induced sterility as a result of tissue specific or whole plant expression of a biotin binding protein. It will be appreciated that in order to report such findings plants expressing the biotin binding protein must develop functional sexual organs. As such, if somatic cell degeneration was effected in such a case, such degeneration would prevent the plant from developing these sexual organs altogether.

As is further detailed hereinunder, cytoplasmic expression of streptavidin, although implicated in producing male sterility does not always produce somatic cell degeneration.

This selective somatic cell degeneration in plants can be influenced by several factors.

First, the biotin level or pool, present in somatic cells can be higher than that present in germline cells. Furthermore in this respect, since biotin exists in the cell in either the free form or in a bound form, the ratio between bound and unbound biotin can vary between somatic and germline cells. As such, expression of a biotin binding protein in a level which is sufficient for causing male sterility may not be sufficient for causing somatic cell degeneration.

Second, it is possible that although expression of a biotin binding protein effects somatic cellular processes to some extent, such an effect does not lead to cellular degeneration. On the other hand, since pollen generation is a complex cellular event, it is possible that interrupting or down regulating some of the cellular processes in germline cells by the depletion of at least a portion of the biotin contained therein is sufficient in preventing normal pollen development and as a result leads to male sterility.

As is further detailed hereinunder, with respect to the examples given, somatic plant cell degeneration utilizing a biotin binding protein can be effected, providing that a careful expression strategy for the biotin binding protein is practiced, which strategy takes into account the following: (i) the endogenous biotin levels of the plant species in which the biotin binding protein is expressed; (ii) the expression level and localization of the biotin binding protein; (iii) the subcellular localization of the biotin pool; (iv) the binding activity between biotin and the biotin binding protein; and (v) the cellular environment, such as pH, and its effect on the binding activity.

As is further detailed in the example given herein, various plant species contain varying levels of biotin. As a direct result, and as further detailed therein, to effect somatic cell degeneration it is imperative that the expression level of the biotin binding protein, which in this case is streptavidin, be correlated to the biotin level of the plant in which it is expressed. Failure to achieve such correlation could result in either total degeneration of the transformed tissues or, on the other extreme, no appreciable degeneration, in either case somatic cell degeneration would not be observed.

As such, when expressing a biotin binding protein within plants for the purposes of somatic cell degeneration, suitable expression vectors must be constructed such that depletion of biotin is sufficient to cause somatic cell degeneration but at the same time allowing plant viability.

As further detailed hereinbelow the method according to the present invention employs suitable expression constructs designed according to an expression strategy further detailed hereinbelow. In addition, suitable transformants are selected for since an expression level results from the promoter, the regulatory elements present in the expression cassette, the copy number and the position of the expression cassette within the genome of the plant.

As used herein and in the claim section that follows the phrase "nucleotide sequence", refers to an oligonucleotide, nucleic acid, or polynucleotide, and fragments or portions thereof, and to DNA or RNA of genomic or synthetic origin which may be single- or double-stranded, and represent the sense or antisense strand. Similarly, "amino acid sequence", as used herein refers to an oligopeptide, polypeptide, or protein sequence, and fragments or portions thereof.

As used herein in the specification and in the claims section that follows the term "transformed" and its conjugations such as transformation, transforming and transform, all relate to the process of introducing heterologous nucleic acid sequences into a cell or an organism, which nucleic acid are propagatable to the offspring. The term thus reads on, for example, "genetically modified", "transgenic" and "transfected", which may be used herein to further described and/or claim the present invention. The term relates both to introduction of a heterologous nucleic acid sequence into the genome of an organism and/or into the genome of a nucleic acid containing organelle thereof, such as into a genome of chloroplast or a mitochondrion.

As used herein the phrase "viral infected" includes infection by a virus carrying a heterologous nucleic acid sequence. Such infection typically results in transient expression of the nucleic acid sequence, which nucleic acid sequence is typically not integrated into a genome and therefore not propagatable to offspring, unless further infection of such offspring is experienced.

There are various methods of introducing foreign genes into both monocotyledonous and dicotyledenous plants (Potrykus, I., Annu. Rev. Plant. Physiol., Plant. Mol. Biol. (1991) 42:205–225; Shimamoto et al., Nature (1989) 338: 274–276). The principle methods of causing stable integration of exogenous DNA into plant genomic DNA include two main approaches:

(i) *Agrobacterium*-mediated gene transfer: Klee et al. (1987) Annu. Rev. Plant Physiol. 38:467–486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2–25; Gatenby, in Plant Biotechnology, eds. Kung, S. and Amtzen, C. J., Butterworth Publishers, Boston, Mass. (1989) p. 93–112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52–68; including methods for direct uptake of DNA into protoplasts, Toriyama, K. et al (1988) Bio/Technology 6:1072–1074. DNA uptake induced by brief electric shock of plant cells: Zhang et al. Plant Cell Rep. (1988) 7:379–384. Fromm et al. Nature (1986) 319:791–793. DNA injection into plant cells or tissues by particle bombardment, Klein et al. Bio/Technology (1988) 6:559–563; McCabe et al. Bio/Technology (1988) 6:923–926; Sanford, Physiol. Plant. (1990) 79:206–209; by the use of micropipette systems: Neuhaus et al., Theor. Appl. Genet. (1987) 75:30–36; Neuhaus and Spangenberg, Physiol. Plant. (1990) 79:213–217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197–209; and Ohta, Proc. Natl. Acad. Sci. USA (1986) 83:715–719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1–9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Sequences suitable for permitting integration of the heterologous sequence into the plant genome are recommended. These might include transposon sequences and the like for homologous recombination as well as Ti sequences which permit random insertion of a heterologous expression cassette into a plant genome.

Suitable prokaryote selectable markers include resistance toward antibiotics such as ampicillin or tetracycline. Other DNA sequences encoding additional functions may also be present in the vector, as is known in the art.

The constructs of the subject invention will include an expression cassette for expression of the protein of interest. Usually, there will be only one expression cassette, although two or more are feasible. The recombinant expression cassette will contain in addition to the heterologous sequence one or more of the following sequence elements, a promoter region, plant 5' untranslated sequences which can include regulatory elements, initiation codon depending upon whether or not the structural gene comes equipped with one, and a transcription and translation termination sequence. Unique restriction enzyme sites at the 5' and 3' ends of the cassette allow for easy insertion into a pre-existing vector.

Viruses are a unique class of infectious agents whose distinctive features are their simple organization and their mechanism of replication. In fact, a complete viral particle, or virion, may be regarded mainly as a block of genetic material (either DNA or RNA) capable of autonomous replication, surrounded by a protein coat and sometimes by an additional membranous envelope such as in the case of alpha viruses. The coat protects the virus from the environment and serves as a vehicle for transmission from one host cell to another.

Viruses that have been shown to be useful for the transformation of plant hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172–189 (1988). Pseudovirus particles for use in expressing foreign DNA in many hosts, including plants, is described in WO 87/06261.

Construction of plant RNA viruses for the introduction and expression of non-viral foreign genes in plants is demonstrated by the above references as well as by Dawson, W. O. et al., Virology (1989) 172:285–292; Takamatsu et al. EMBO J. (1987) 6:307–311; French et al. Science (1986) 231:1294–1297; and Takamatsu et al. FEBS Letters (1990) 269:73–76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression of non-viral foreign genes in plants is demonstrated by the above references as well as in U.S. Pat. No. 5,316,931

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired protein.

A technique for introducing heterologous nucleic acid sequences to the genome of the chloroplasts is known. This technique involves the following procedures. First, plant cells are chemically treated so as to reduce the number of chloroplasts per cell to about one. Then, the heterologous nucleic acid is introduced via particle bombardment into the cells with the aim of introducing at least one heterologous nucleic acid molecule into the chloroplasts. The heterologous nucleic acid is selected such that it is integratable into the chloroplast's genome via homologous recombination which is readily effected by enzymes inherent to the chloroplast. To this end, the heterologous nucleic acid includes, in addition to a gene of interest, at least one nucleic acid stretch which is derived from the chloroplast's genome. In addition, the heterologous nucleic acid includes a selectable marker, which serves by sequential selection procedures to ascertain that all or substantially all of the copies of the chloroplast genomes following such selection will include the heterologous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

As used herein and in the claims section which follows the term "transgenic" when used in context of a plant, plant derived tissues or plant cells refers to the existence therein of an exogenously introduced nucleic acid sequence, which sequence can include an expression cassette and flanking nucleic acid sequences encoding, for example, antibiotic resistance, origin of replication and the like.

As used herein and in the claims section which follows, the term "expression cassette" refers to a nucleic acid sequence which encodes, for is example a promoter, regulatory elements and a region coding for a translatable or non-translatable RNA molecule.

As used herein and in the claims section which follows, the term "heterologous" when used in context of a nucleic acid sequence or a protein found within a plant, plant derived tissue or plant cells, refers to nucleic acid or amino acid sequences typically not native to the plant, plant derived tissue or plant cells.

As used herein and in the claims section which follows, the phrase "plant signal peptide" refers to a stretch of amino acids which is effective in targeting a protein expressed in a plant cell into the endoplasmic reticulum. Targeting a protein into the endoplasmic reticulum typically leads to one of five alternate outcomes. The protein can be directed for secretion into the apoplast (vesicles mediate secretion), targeted into the lysosome for destruction, targeted into other intracellular vesicles for storage or function, targeted into the cell membrane or targeted into membranes of cellular compartments.

As used herein and in the claims section which follows, the phrase "bacterial signal peptide" refers to a stretch of amino acids which is naturally effective in secreting a protein out of a bacterial cell.

As used herein and in the claims section that follows, the phrase "plant leader peptide" refers to a stretch of amino acids which is naturally effective in targeting a protein into a DNA containing organelle of a plant cell.

As used herein and in the claims section which follows, the phrase "DNA containing organelle" refers to mitochondria and chloroplasts.

As used herein and in the claims section which follows the phrase "plant essential factor" refers to a plant cellular factor which participates in, for example, metabolic, and/or signal transduction pathways, such as, but are not limited to, metal ions, vitamins and the like, which typically serve as catalysts, co-enzymes and the like. In addition, plant essential factors can form a part of structural elements or assist in forming or maintaining a linkage between molecules. Depletion of these factors from a plant cell or tissue leads to "cell degeneration" or "tissue degeneration" which are used herein to describe the process in which cellular viability gradually diminishes to the point of cell/tissue death. Such "cell degeneration" or "tissue degeneration" can be reversed prior to cell or tissue death by external application of the depleted plant essential factor.

As used herein and in the claims section that follows, the phrase "antisense RNA", refers to an RNA sequence which is complementary to a specific DNA or RNA sequence. Antisense RNA may be produced by any method, including synthesis by ligating the gene(s) of interest in a reverse orientation to a promoter which permits the synthesis of a complementary strand. Once introduced into a cell, the transcribed RNA combines with natural sequences produced by the cell to form duplexes. These duplexes then block either the further transcription or translation or leads to mRNA degradation.

As used herein and in the claim section that follows, the term "ribozyme", refers to an RNA sequence having an RNase catalytic activity. A ribozyme preferably includes also an antisense RNA sequence so as to exert its catalytic activity on complementary messenger RNA (mRNA) molecules.

As used herein and in the claims section that follows, the term "somatic" when used in context of plant tissues or cells refers to both vegetative and reproductive plant tissues or cells and as such includes the entire plant other than the sex cells (pollen and oocyte) or their progenitors As used herein, the phrase "regulatory element" refers to nucleotide sequences which are typically included within an expression cassette and function in regulating (i.e., enhancing or depressing) the expression therefrom. This regulation can be effected either at the transcription or the translation stages. Examples of regulatory elements include, but are not limited to, an enhancer, a suppresser and a transcriptional terminator.

As used herein and in the claims section that follows, the term "plant promoter" refers to a promoter which can direct gene expression in plant cells. Such a promoter can be derived from a plant, a plant virus, or from any other living organism including bacteria and animals.

The promoter can be a constitutive promoter, such as, but not limited to, CaMV35S and CaMV19S promoters, FMV34S promoter, sugarcane baciliform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

The promoter can alternatively be a tissue specific promoter. Examples of tissue specific promoters include, without being limited to, bean phaseolin storage protein promoter, DLEC promoter, PHSβ promoter, zein storage protein promoter, conglutin gamma promoter from soybean, AT2S1 gene promoter, ACT11 actin promoter from *Arabidopsis*, napA promoter from *Brassica napus*, potato patatin gene promoter and the Tob promoter.

The promoter may also be a promoter which is active in a specific developmental stage of the plant's life cycle, for example, a promoter active in late embryogenesis, such as: the LEA promoter, (Hughes and Galau, 1989 and 1991, Galau, et al., 1991, 1992 and 1993); Endosperm-specific expression promoter (the seed storage prolamin from rice is expressed in tobacco seed at the developmental stage about 20 days after flowering) (Zhou and Fan, 1993) or the promoter controlling the FbL2A gene during fiber wall synthesis stages (Rinehart et al., 1996).

In case of a tissue-specific promoter, it ensures that the heterologous protein, or antisense RNA are expressed only in the desired tissue, for example, only in the flower, the root, the seed, etc.

In case of a developmental-tissue specific promoter the heterologous protein or antisense RNA are expressed only during a specific stage of the plant as the tissue is degenerated only in that stage.

Both the tissue-specific, and the non-specific promoters may be constitutive, i.e., may cause continuous expression of the heterologous protein or antisense RNA.

The promoter may also be an inducible promoter, i.e., a promoter which is activated by the presence of an inducing agent, and only upon said activation, causes expression of the heterologous protein or antisense RNA. An inducing agent can be for example, light, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, the promoters hsr303J and str246C active in pathogenic stress, the copper-controllable gene expression system (Mett et al., 1993) and the steroid-inducible gene system (Schena et al., 1991).

Alternatively, an inducing agent ma) be an endogenous agent which is normally present in only certain tissues of the plant, or is produced only at certain time periods of the plant's life cycle, such as ethylene or steroids. By using such an endogenous tissue-specific inducing agent, it is possible to control the expression from such inducible promoters only in those specific tissues. By using an inducing agent produced only during a specific period of the life cycle, it is possible to control the expression from an inducible promoter to the specific phase in the life-cycle in which the inducing agent is produced.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of effecting degeneration of somatic plant tissue. The method is effected by expressing in somatic plant cells a heterologous protein capable of binding a plant essential factor, such as, for example, biotin. The heterologous protein is expressed from an expression cassette which includes the polynucleotide sequence encoding the heterologous protein and flanking regulatory sequences, which are further discussed hereinbelow, and which enable the expression of the heterologous protein from the polynucleotide sequence following introduction of the expression cassette into plant cells.

It will be appreciated that the introduction of the expression cassette into plant cells, plant tissues or a whole plant can be effected by several approaches. For example, stable transformations, wherein the expression cassette is integrated into the genome of the host cell, following which the host cell is regenerated into a whole plant can include, but is not limited to, *Agrobacterium* mediated plant transformation, biolistic bombardment, electroporation and the like. Using these approaches a plant can be generated in which all the cells contain a stably integrated copy or copies of the expression cassette. Since the expression cassette of these plants is stably integrated into the genome of its cells, including germline cells, it is transferred to the offsprings thereof.

Alternatively, transient transformation of plant cells, plant tissues or a whole plant can be effected by approaches which enable the expression of the heterologous protein in a transient manner. As used herein the phrase "transient transformation" refers to expression which is dependent on the existence of the expression cassette within the nucleoplasm or cytoplasm of the expressing cells. When effecting transient transformation the expression cassette is not stably integrated into the host cell genome and as such the expression cassette is not transferred to offsprings of the transiently transformed plant.

Transient transformation can be effected by several approaches which can include, but are not limited to, biolistic bombardment, *Agrobacterium* mediated transient transformation, electroporation and recombinant viral infection using plant viruses which can include, but are not limited to, tobacco mosaic virus (TMV), potato virus X (PVX) and the like. Typically, biolistic bombardment and electroporation can be used to transform limited region of the somatic tissue or single cell of a cell culture. On the other hand, recombinant viral infection is also applicable for producing whole plant expression since host specific viruses can be employed to systematically infect a plant. Not withstanding from the above, it will be appreciated that in such cases a portion of the systematically infecting recombinant virus can infect germline cells and mature seeds and as such be transferred to offsprings of the infected plant.

As is further detailed hereinbelow iii the Examples section with respect to biotin depletion, a correct level of depletion of the plant essential factor is crucial in order to effect somatic cell degeneration, but at the same time, maintain plant viability. To achieve this, an expression strategy of the heterologous protein, must be planed accordingly. As such when planning a suitable expression strategy for the heterologous protein one or more of the following criteria must be taken into account: (i) a level of expression of the heterologous protein; (ii) a distribution of the heterologous protein in the plant tissue; (iii) binding activity of the heterologous protein with the essential factor; (iv) abundance and distribution of the essential factor in the cells; and (v) a level of the factor externally provided to the somatic plant tissue.

The level of expression is typically influenced by the promoter used to drive the expression of the heterologous protein, by the copy number of the expression cassette within the plant cell genome or the plant nucleoplasm or cytoplasm and in some cases, by the codon usage of the expressed polynucleotide sequence and by what is known as positional effect and/or co-suppression. By selecting a suitable promoter the resultant level of expression can be predetermined, such a suitable promoter is selected from any of the promoter types listed hereinabove. The promoter can also be used in combination with a regulatory element. By selecting stably transformed plants with a predetermined optimal copy number, or by transiently transforming plant somatic tissue with an optimal copy number of the expression cassette, the level of somatic tissue degeneration can also be predetermined.

The distribution of the heterologous protein in the plant tissue can also be controlled. For example if a plant essential factor is concentrated or active in a subcellular organelle, e.g., a DNA containing organelle, such as a chloroplast or mitochondria, the heterologous protein can be expressed within this organelle either by organelle transformation or alternatively by the use of a leader peptide of organelle targeting. Targeting can also be to other cellular constituents, such as the endoplasmic reticulum, or to secretion.

In addition since a somatic plant tissue is composed of various cell types, a tissue specific promoter can be used which is only operative in certain cell types of the various cell types such that selective degeneration of these cell types can be effected.

Consideration must also be given to the binding activity of the heterologous protein with the essential factor. It will be appreciated that in cases were a high affinity and/or strong binding is exhibited between the heterologous protein and the plant essential factor, the level of expression of the heterologous protein must be adjusted so as to achieve the balance between somatic cell degeneration and plant viability. It will be appreciated that binding activity can also be influenced by the pH and other factors of the cellular or subcellular environment, thus when planning an expression strategy consideration to the influence of the pH on the binding activity can be given.

The abundance of the essential factor in the cells is also a parameter which must be considered when expressing a heterologous protein. As is clearly demonstrated for biotin in the examples given below, different plant species exhibit different levels of this plant essential factor. Furthermore, the level of the plant essential factor may charge throughout development stages of a plant, or it may be influenced by environmental parameters such as water, light conditions, soil conditions and the like.

Finally, as is further detailed hereinbelow, regeneration of degenerated somatic tissue is at times preferred and as such consideration to the ability of effecting such regeneration, by, for example, externally supplementing the plant essential factor, must also be given.

It will be appreciated that although the considerations are valid, one may find it difficult to consider such considerations in advance. However, knowing these considerations, one can understand the results one obtains, so as avoid unwanted results in following trials.

One can determine the outcome of the combination of the above criteria by simple experimentation, such as, but not limited to, monitoring the expression level of the heterologous protein and its activity and distribution, monitoring plant growth or determining a dose response of regeneration of degenerated plant tissue by external application of the essential factor.

One can therefore select individual plants which show preferred characteristics.

According to a preferred embodiment of the present invention the degeneration of somatic plant tissues can be reversed by introducing into the degenerated tissue a neutralizing agent which can be effected by any one of the following approaches:

(i) co-expressing within a plant a second expression cassette which transcribes either, a ribozyme capable of degrading the mRNA encoding the heterologous protein, or an antisense strand of the mRNA encoding the heterologous protein.

(ii) co-expressing within a plant a second expression cassette which encodes for an antagonist protein which is capable of preventing or interrupting the binding of the heterologous protein with the plant essential factor.

These neutralizing agents are preferably expressed in a controlled manner by using, for example, an inducible promoter such that their neutralizing action can be regulated in a temporal, spatial and quantitative manner.

(iii) restoring to the degenerated tissue or to a whole plant normal levels of the plant essential factor. This is achieved by externally applying the plant essential factor to the plant or plant tissue, preferably in the presence of a surfactant such that the plant essential factor readily permeates into the cells. Alternatively, the plant essential factor can be introduced into the plant through the roots thereof.

In addition regeneration of degenerated somatic plant cells can be effected by down regulating the expression of the heterologous protein. For example, if the heterologous protein is expressed from an inducible promoter which necessitates the presence of an external factor to induce expression (see hereinabove for further description), removing the external factor down regulates this promoter such that expression is not induced therefrom and regeneration is thus effected.

Finally, the regeneration of degenerated somatic plant tissue can also be effected by up-regulating the biosynthesis or transport of the plant essential factor within the plant. This can be achieved by introducing into the plant a polynucleotide sequence coding for a protein or proteins involved in the biosynthesis or transport of the plant essential factor. Alternatively, the plant essential factor can be upregulated externally by for example, applying an external agent (e.g., plant hormone) other than the plant essential factor, which leads to upregulation of the plant essential factor within the plant.

As is clear from the arguments presented hereinabove several criteria must be taken into account such that somatic cell degeneration is effected while at the same time plant viability is maintained.

The result of practicing the method of the present invention as herein described in a transgenic plant expressing a heterologous protein capable of binding a plant essential factor. The level, distribution, etc., of the heterologous protein is selected in accordance with the above established considerations, so as to lead to the depletion of the essential factor to a level such that plant viability is maintained, while at the same time, degeneration of somatic plant tissue is effected.

The method of degenerating plant somatic tissue according to the present invention can be utilized, for example, to selectively degenerate plant somatic tissue to thereby control the morphology of a plant. This can be effected by expressing in somatic cells of the plant a heterologous protein capable of binding a plant essential factor while taking into account the criteria established hereinabove. Once degeneration is observed, a selected portion of the degenerated tissue can be regenerated by introducing any of the neutralizing agents described hereinabove to a selected portion of the degenerated somatic tissue. The neutralizing agent is capable of reversing the depletion of the plant essential factor and is therefore leading to the regeneration of the selective portion of the degenerated somatic tissue. It will be appreciated that the above mentioned method can also be applied to plant tissue culture, callus tissue and explants to effect degeneration and optional regeneration of selected individual cells. Thus, as used herein the term "plant" refers also to plant cells, clusters thereof and to plant calli.

As already mentioned hereinabove, selective degeneration can also be effected by employing a tissue specific promoter to thereby express the heterologous protein in a selected portion of the somatic plant tissue.

It will be appreciated that the above mentioned methods can also be used to regulate plant growth by either introducing a neutralizing agent to selected portion(s) of the plant somatic tissue during developmental stages or by expressing the heterologous protein under the control of a developmentally regulated promoter.

According to a preferred embodiment of the present invention the plant essential factor is biotin.

As already mentioned hereinabove, biotin is an essential cofactor for a variety of carboxylases and decarboxylases which participate in diverse metabolic pathways in both the cytoplasm and subcellular organelles of plant cells. As such, controlled expression of a biotin binding protein in somatic plant cells causes biotin depletion and subsequently leads to somatic cell degeneration. Thus, according to another preferred embodiment of the present invention the heterologous protein is avidin, streptavidin or functional derivatives thereof.

Streptavidin, is the preferred biotin-binding protein according to the present invention. Streptavidin is a tetrameric protein, having four identical subunits, and is secreted by the actinobacterium *Streptomyces avidinii*. Both streptavidin, and its functional homologue avidin, exhibit extremely tight and highly specific binding to biotin which is one of the strongest known non-covalent interactions between proteins and ligands. Although avidin and streptavidin have almost the same high affinity for biotin, they are different in many other respects. The two proteins have different molecular weights, electrophoretic mobilities and overall amino acid composition. Avidin is a glycoprotein found in egg whites and the tissues of birds, reptiles and amphibians. Like streptavidin, avidin has almost the same high affinity for biotin and exists as a tetramer. Avidin contains carbohydrates which cause it to bind non-specifically to biological materials including cell nuclei, nucleic acids and lectins. Due to these non-specific interactions avidin is less suitable than streptavidin for utilization as a biotin binding protein to effect somatic plant cell degeneration according to the teachings of the present invention. However, the use of avidin while practicing the present invention is not ruled out.

It was demonstrated by the study conducted while reducing the present invention to practice that specific sequences of streptavidin in combination with flanking non-streptavidin sequences are most suitable for effecting somatic cell degeneration while maintaining plant viability. As such, according to a preferred embodiment of the present invention the heterologous protein is one of the proteins set forth in SEQ ID NOs:2 or 6.

According to another preferred embodiment of the present invention a biotin binding heterologous protein is expressed within or targeted into a DNA containing organelle, such as mitochondria or chloroplasts. It will be appreciated that since biotin participates in metabolic pathways present within these organelles, practicing the above approach would lead to somatic cell degeneration. In fact, since the biotin pool present within these organelles is a relatively small portion of the total cellular biotin, a lower level of expression or lower binding and/or affinity of the biotin binding protein is necessary to effect degeneration. As a direct result, a partially functional fragment of the biotin binding protein, or alternatively a mutant thereof which displays lower binding to biotin than the native protein can also be used.

As already mentioned above, reversal of the degeneration of plant somatic tissue can be effected by several methods. In the case of biotin depletion, reversal can be readily effected by applying biotin directly to the plant as is further described hereinbelow in the Examples section.

It will be appreciated that many other essential factors exist in plant cells. The depletion of such factors by their respective heterologous binding proteins can be used to controlled somatic cell degeneration in plants.

Thus according to another preferred embodiment of the present invention the plant essential factor can be, but it is not limited to, ions of, for example, iron, zinc and calcium, and a factor such as thiamin. When selecting appropriate plant essential factors careful consideration is to be given to the criteria listed hereinabove.

Each of these plant essential factors can be selectively depleted from the plant cell by utilizing a specific heterologous binding protein.

For example, iron can be directly depleted from somatic plant cells by expressing within these cells, an iron binding protein such as ferritin.

Ferritins are high molecular mass multimeric proteins which can accommodate up to 4500 iron atoms in their central cavity (Theil et al., 1987, Harrison et al., 1989, Andrews et al., 1992). The uptake and release of iron by this protein fulfills metabolic iron requirements, avoids insolubility and eliminates toxicity of this element in the presence of Oxygen. Plant ferritins are found within plastids, and their regulation has been shown to take place at the transcriptional level (Lecure et al., 1991). A study by Van Wuytswinkle et al., (1998) has shown that expression of soybean ferritin either in the cytosol or plastids of tobacco plants leads to iron sequestration resulting in iron deficiency. Although these plants upregulate iron uptake from the roots in response to this iron deficiency, some cellular damage, such as chlorotic lesions and an overall decrease in soluble protein concentration was observed.

Calcium can also be selectively depleted from somatic plant tissue, by expressing within the plant a calcium binding protein or a calcium binding portion thereof.

Calcium primarily functions in stabilizing reversible intermolecular linkages, predominantly in the cell wall and in the plasma membrane. Calcium is found throughout the plant cell although a large concentration exists in the mitochondria. Depletion of calcium results in what is termed as calcium-deficiency related disorders in tissue development.

One example of a calcium binding protein is calmodulin. Calmodulin is a primary $Ca^{2+}$-binding protein found in all eukaryotic cells. It couples the intracellular $Ca^{2+}$ signal to many essential cellular events by binding and regulating the activities of more than 40 different proteins and enzymes in a $Ca^{2+}$-dependent manner. It will be appreciated that since calmodulin participates in cellular events in plant cells by interacting with intracellular proteins and enzymes, expression of calmodulin within somatic plant cells can lead to undesirable effects. As such, only a $Ca^{2+}$ binding domain or portion of calmodulin is preferably expressed within somatic plant cells to effect degeneration. This domain or portion can also be fused to a carrier protein and expressed as a chimeric protein if the native protein folding has to be mimicked for activity. Alternatively, mutants of calmodulin which have lost their ability to interact with intracellular proteins and enzymes, but still bind $Ca^{2+}$ can also be utilized by the present invention to effect degeneration.

A zinc binding protein or a zinc binding portion or domain thereof such as for example, a zinc finger, a zinc cluster, or a zinc twist can also be utilized as a plant essential factor binding protein by the present invention.

Zinc is required for the activity of various types of enzymes including dehydrogenases, aldolases, isomerases, transphophorylases and polymerases. Therefore, zinc deficiency is often associated with impairment of carbohydrate metabolism and protein synthesis. Effects of zinc deficiency include stunted growth, decreased leaf size, leaf chlorosis and shortening of internodes.

Numerous examples of zinc binding proteins from animals and from plants exist in the art. Zinc binding domains have been well characterized and sequences of several such domains are well known in the art. As such, one ordinarily skilled in the art could easily construct a chimeric protein which includes, for example, a carrier protein fused to a zinc binding domain to effect controlled somatic cell degeneration according to the present invention.

Thiamin binding proteins have also been described in the art. For example, Watanabe et al., 1998, describes the isolation and characterization of a thiamin-binding protein from sunflower seeds. Thiamin is a plant essential factor which participates in various cellular events and metabolic pathways. As such, depletion of thiamin by expression of a thiamin binding protein or any thiamin-binding portion or domain thereof can in effect lead to the degeneration of somatic plant tissue.

It will be appreciated by one ordinarily skilled in the art that binding proteins for other plant essential factors such as, for example, Mg ions and Ni ions can be isolated and characterized using methods which are well known in the art. These isolated proteins can then be used to effect controlled somatic cell degeneration in accordance with the teachings of the present invention.

Thus, by carefully planning an expression strategy for the above exemplified essential factor binding proteins while taking into account the criteria established hereinabove, the selective depletion of essential factors, such as, but not limited to, ions of iron, calcium and zinc, and factors such as biotin and thiamin, can be effected such that controlled and optionally reversible somatic cell degeneration ensues. It will be appreciated that degeneration effected by such binding proteins can be reversed by any of the neutralization approaches mentioned hereinabove. For example, regeneration of Ca, Zn and Fe deficient tissues can be effected through an external application of these plant essential factors by, for example, spraying of inorganic salts of these ions preferably provided in a solution containing a surfactant.

According to the teachings of the present invention selective/controlled degeneration and optionally regeneration of somatic plant tissue can be utilized to effect the following: (i) decrease the number of flowers in fruit producing plants so as to increase the number of fruits which reach maturity; (ii) decrease the number of fruits so that each fruit produced is larger; (iii) degenerate seeds so that they are unable to germinate in order to avoid growing of new crops by unauthorized persons in possession of the parent plants; (iv) produce seedless fruits; (v) modify flower shape by altering the biogenesis of the floral tissue; (vi) modify and/or arrest the development of somatic tissue in order to reduce the need for clipping, shearing, trimming, pruning, cutting, etc.; (vii) postpone/delay or eliminate flowering in forage crops to extend the vegetative growth of the plant. (viii) block or reduce successful penetration and colonization of plant pathogens (like *Orobanche* spp.) by reducing or arresting the viability of invaded cells; (ix) generate dwarfed plants with numerous stems and a bushy phenotype with no growth retardation inflicted upon the individual stems, this is especially applicable under "space limited" growth conditions; (x) use of the degenerating characteristic phenotype as a reporter gene in promoterless trapping cassettes and to localize expression of genes and promoters in plants; (xi) generate flowering plants which do not produce fruit by expressing the essential factor binding protein in the flower's stigma, this is desirable, for example, in ornamental plant cultivation since it considerably prolongs flower shelf-life.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., molecular Cloning—A Laboratory Manual, Cold Spring Harbor Laboratory, Cold Spring Harbor, N.Y. (1989), which is incorporated herein by reference. Other general references are provided throughout this document. The procedures therein are believed to be well known in the art and are provided for the convenience of the reader. All the information contained therein is incorporated herein by reference.

While conceiving the present invention, it was hypothesized that since streptavidin can bind free- and bound biotin (e.g., biotinylated proteins) substantially irreversibly, its expression in a somatic plant cell in a suitable expression level may cause cell degeneration. In an attempt to find a way to express streptavidin in planta and to study its effects, several artificial streptavidin gene expression cassettes were constructed and tested for toxicity in transient expression assays. The streptavidin construct which caused the least damage to the plant tissue, but yet caused the visible degeneration of this tissue was subsequently used to genetically transform tomato plants.

Materials and Experimental Methods

Plant Growth Conditions:

Tomato plants were grown in a glass greenhouse with natural light and controlled temperature of 25–30° C. Tissue cultures and germination of seeds were performed in controlled rooms under 12 hours photoperiod (white light) at 25° C.

Determination of Plant-Biotin Content:

Biotin content of plants was determined according to a method developed by the Inventors. Ten μl samples of leaf extracts were placed on a layer of soil bacteria auxotrophic for biotin, that were spread on solidified M-9 media (Sambrook et al., 1989). Bacterial growth obtained was proportional to the amount of biotin in the extract samples and was compared to the growth obtained with biotin standards. Results were normalized according to the protein concentration in each sample as was determined by Bradford assay (Bradford 1976).

PCR Amplification of Bacterial Streptavidin:

PCR amplification was performed using a BamHI genomic fragment of *Streptomyces avidinii* (50 ng, Gene Bank accession No. x03591) as a template, and 10 pmole of direct and reverse primers as listed in Table 1 according to the primer combinations lists in Table 2. Following denaturation for 3 minutes at 95° C., 36 amplification cycles of 30 seconds at 94° C., 45 seconds at 59° C. and 45 seconds at 72° C. with a final 5 minutes extended elongation step were effected in a PTC-100 Programmable Thermal Controller (MJ Research Inc. USA). The PCR product was gel purified, cloned in pGEM-T (Promega) and sequenced.

TABLE 1

*Streptavidin* primers

| Primer | SEQ ID | Primer sequence | nt |
|---|---|---|---|
| streptavidin-d | 15 | 5'-actgcagttATGCGCAAGATCGTCG-3' | 50–65 |
| streptavidin-r | 16 | 5'-GACTACTGCTGAACGGCG-3' | 603–585 |
| mst | 17 | 5'-*gtaaacaatggct*CGCAAGATCGTCGTTGCAG-3' | 52–71 |
| prost | 18 | 5'-*gactgcagtt*GACCCCTCCAAGGACTCGAAGGCCCAG-3' | 122–148 |
| mprost | 19 | 5'-*gtaaacaatggct*GACCCCTCCAAGGACTCGAAGGCCCAG-3' | 122–148 |
| cstreptavidin-d | 20 | 5'-actgcaGGCATCACCGGCACCTGGTACAAC-3' | 166–190 |

TABLE 1-continued

Streptavidin primers

| Primer | SEQ ID | Primer sequence | nt |
|---|---|---|---|
| cstreptavidin-r | 21 | 5'-CTACGGCTTCACCTTGGTGAAG-3' | 527–508 |
| cyto | 22 | 5'-*gtaaacaatggct*GGCATCACCGGCACCTGGTACAAC-3' | 166–190 | nt- corresponding nucleic acids in streptavidin gene (accession No. x03591)
d- direct primer.
r- reverse primer.
lower case- PstI restriction site.
lower case, italics- translation start site (Lutche et al., 1987).
upper case- streptavidin sequences.

TABLE 2

Primer combinations used to produce streptavidin artificial genes

| Designation | Direct Primer | Reverse Primer |
|---|---|---|
| sps | streptavidin-d | streptavidin-r |
| mst | mst | streptavidin-r |
| prost | prost | streptavidin-r |
| mprost | mprost | streptavidin-r |
| cst | cstreptavidin-c | cstreptavidin-r |
| cyto | cyto | cstreptavidin-r |

DNA Sequence Analysis:

The two strands of each streptavidin-PCR fragment cloned in pGEM-T (Promega) or signal peptide-streptavidin chimera cloned in pBluescript SK(-) (Stratagene) were sequenced by the dideoxy chain termination method using an automated DNA sequencer, dye terminators, and the standard T3, T7 and/or sp6 primers. Computer analyses of nucleic acid and amino acid sequences were carried cut using software from the GCG/EGCG package of the University of Wisconsin running under a UNIX system.

Construction of Chimeric Streptavidin:

The PCR products sps (SEQ ID NO:1), prost (SEQ ID NO:5) and cst (SEQ ID NO:9), cloned in the pGEM-T vector were recloned as PstI fragments in-frame to signal peptide for secretion, originated from wheat gene for α/β-gliadin storage protein (SEQ ID NO:14) (pW 8233) (Gene Bank accession No. x02539). These signal peptide-fused chimeric segments as well as the PCR fragments mst (SEQ ID NO:3), mprost (SEQ ID NO:7) and cyto (SEQ ID NO:11), were ligated between CaMV35S promoter (Gene Bank accession No. E01311) and NOS terminator (Gene Bank accession No. X74123) to create plant expression cassettes. These cassettes were cloned into pBin+ vector (Van Engelen et al., 1995) and were used for tomato transformation mediated by *Agrobacterium* EHA 105 (Hood et al., 1993).

Transient Expression Assay:

*Agrobacterium* containing the streptavidin constructs were grown for 20 hours in liquid YEB media, pH 7.0, at 28° C., and were transferred to fresh YEB pH 5.2 for a subsequent 4 hours incubation period. Bacterial cells were precipitated by centrifugation (500 rpm, 10 minutes at room temperature), suspended in a solution containing Murashige and Skoog (MS) salts and 2% sucrose and infiltrates into 7–10 day-old tomato seedlings (VF-36), by applying a two minute vacuum followed by further incubation at room temperature for 15 minutes. Co-cultivation was performed for 3–4 days on 1 MM Whatmann paper discs placed on solidified media containing Murashige and Skoog (MS) salts, 2% sucrose, 1% glucose, 0.25 gelrite and 100 μM acetosyringone, pH 5.2. The seedlings were washed with MS solution containing 2% sucrose to remove the *Agrobacterium* and were transplanted in a solidified media containing MS, 3% sucrose, 0.25% gelrite, 0.5 mg/liter zeatin and 300 mg/liter claforan, pH 5.8. Tissue degeneration was initially observed 48 hours following seedling transplantation.

Plant Transformation:

Tomato plants (VF-36 cultivar) were transformed using the leaf disk transformation method with a construct containing the sps expression cassette. Plantlets that were rooted on 100 mg/liter Kanamycin and were further analyzed by PCR using both nptII primers (direct primer 5'-CACGCAG-GTTCTCCGGCCGC-3' (SEQ ID NO:23); reverse primer 5'-TGCGCTGCGAATCGGGAGCG-3' (SEQ ID NO: 24) and the streptavidin primers (Table 1).

Germination Test:

Tomato seeds were sterilized by incubation in 1% (v/v) hyperchloride for 7 minutes and successive five washings with sterile water. Sterile seeds were applied on solidified MS media containing 300 ppm kanamycin and biotin at a concentration of 2 mg/liter. Kanamycin resistant/sensitive seedlings were analyzed one month later.

Northern Blot Analysis:

Total RNA was isolated from young leaves of transgenic tomato and wild type strain using the Tri-Reagent kit (Molecular Research Center Inc., USA). Samples of 10 μg total RNA were separated on a 1.1% formamide-agarose gel (Sambrook et al., 1989), blotted onto a nylon membrane (Hybond N, Amersham, UK), and hybridized with $^{32}$P-sps cassette or with 1-kb tomato $^{32}$P-rDNA fragment (28S). Hybridization was carried out at 65° C. in 0.263 M $Na_2HPO_4$, 1% (w/v) BSA, 7% (w/v) SDS and 1 mM EDTA. The membrane was washed twice with 2×SSC, 0.1% (w/v) SDS at room temperature for 10 minutes, and twice with 0.2×SSC, 0.1% (w/v) SDS at 60° C. for 10 minutes. The blot was exposed to either a Biomax X-ray film (Kodak) with an intensifying screen at −70° C., or a Phosphor-Imager screen. The Phosphor-Imager Program (Fujix BAS 1500, Fuji, Japan) was used for radioactivity quantification.

Southern Blot:

Genomic DNA was isolated from young leaves of transgenic tomato plants and of the wild type strain (VF-36) according to Chee et al., (1991). For Southern blot analysis, 10 μg DNA was digested with EcoRI, separated on a 0.8% agarose gel in Tris-acetate (TAE buffer and blotted onto a Hybond-N$^+$ membrane (Amersham, UK). The membrane was hybridized with the $^{32}$P-760 bp PCR fragment of nptII fragment labeled by random priming. Hybridization, washing and blot exposure conditions were as described for Northern analysis.

Experimental results

Estimation of Biotin Content of Crop plants:

The biotin content of several crop plans was determined using the bacterial assay described hereinabove (FIG. 1). Tobacco was found to contain the highest biotin concentration among the tested plants. Tomato contains approximately half that amount, whereas alfalfa, melon, watermelon, and cucumber contain an even lower concentration of biotin.

Transient Expression of Streptavidin Constructs:

To find the optimal streptavidin chimera for transformation of tomato, transient expression study was conducted. Tomato seedlings were co-cultivated with *Agrobacterium* containing different constructs of streptavidin (FIG. 2) or with vector that does not contain streptavidin sequences (pME).

All streptavidin constructs utilized except for sps and prost caused sever necrotic lesion development in expressing plants. The sps construct and to a lesser extent the prost construct caused only a few brown spots on the stems and cotyledons of expressing plants. The toxicity of the various expression constructs was scaled according to the phenotypes described above and according to the percentage of seedlings that were affected (Table 3). It was concluded that the sps construct is suitable for transformation of tomato plants, as it would enable the plants to complete full life cycle, while at the same time cause degeneration of somatic tissues in which this construct is expressed.

TABLE 3 toxicity scale of the streptavidin constructs

| Construct | toxicity | % cotyledons | % stems | % total seedlings |
|---|---|---|---|---|
| PME (control) | 0 | 0 | 0 | 0 |
| prost | 1 | 39.4 | 0 | 79 |
| sps | 2 | 39.5 | 29 | 79 |
| mprost | 3 | 37.5 | 35 | 75 |
| mst | 4 | 50 | 25 | 100 |
| cyto | 5 | 52 | 33 | 100 |
| cst | 6 | 62.5 | 42 | 100 | a-toxicity rate of the constructs
b-% of affected tissues/seedlings.

Figure 5A:
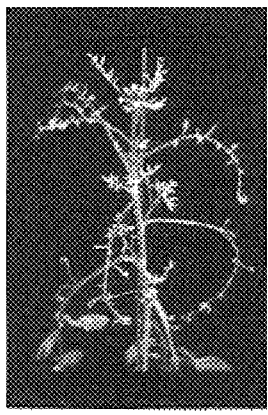
FIG. 5a represents a plant having non vital young chlorotic leaves. Application of biotin solution restored normal leaf development as can be seen 10 days after application (FIG. 5b), or 20 days after initial application (FIG. 5c).
Figure 5A:

Transgenic Tomato Plants:

Tomato plants were transformed with the sps construct, and 34 plantlets that were found to contain the transgene were transferred to the greenhouse. Twenty-four plants suffered of severe stem degeneration at the stage of four true leaves, and died. During the development of the remaining transgenic tomato plants, relatively minor stem and leaves degeneration could be observed in four plants, however, to a different level and time of appearance in the development of these plants (FIG. 5a and Table 4).

TABLE 4

Description of transgenic tomato symptoms

| Transgenic plant | Description of degenerated tissue | Time of appearance |
|---|---|---|
| 2 | Rapid stem degeneration | Prior to flowering |
| 3 | Restricted degeneration areas on stem | Post fruiting |
| 5 | Stem degeneration | During 1st fruit development |
| 13 | Stem and leaves degeneration, defected flower-buds. | Very young plant |
| 1,6,7,8,10,11 | no symptoms | |

Figure 5B:
FIG. 5 demonstrates regeneration of degenerated somatic plant tissue in a T0 plant expressing the sps streptavidin cassette by external addition of biotin. Transformed plant cells were grown in culture in the presence of biotin until T0 plants were developed. The T0 plants were transferred to soil without further biotin supplementation. Within a month (FIG. 5a) severe plant somatic tissue degeneration was evident.
Figure 5B:
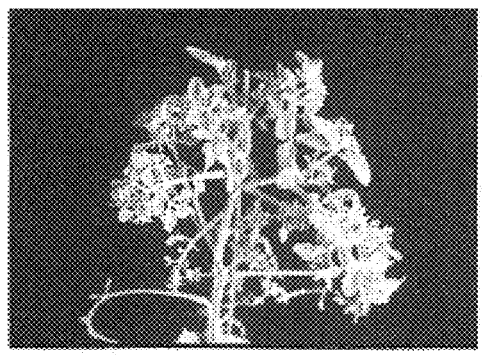
Figure 5C:
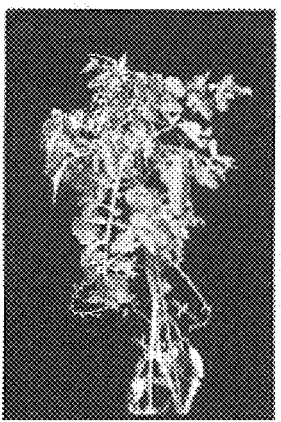
Figure 5C:
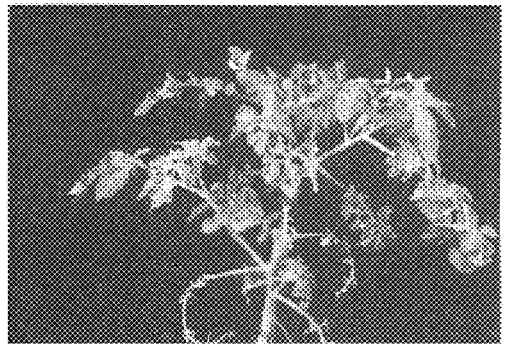

Spraying of 6 mg/liter biotin on the affected area, stopped the degeneration process and plants' growth was restored (FIGS. 5b and 5c). Without spraying of biotin, the plants were completely degenerated, indicating that the phenotype observed was related to the streptavidin expression. The morphology and development of leaves of 6 weeks old plants obtained from non transgenic plant and transgenic tomato plants expressing the sps streptavidin construct and treated daily with biotin were also examined. FIG. 7 depicts the results of this study. Transgenic plants expressing the sps streptavidin construct and treated once (after 3 weeks) with biotin and transgenic plants expressing the sps streptavidin construct and not treated with biotin showed severe morphological changes resultant from tissue degeneration. This degeneration was to a lesser degree in the treated plants. Non transgenic plants both biotin treated and untreated appeared normal.

In addition, seed and fruit development was examined in transgenic plants expressing the sps streptavidin cassette under the Tob promoter (Yamamoto et al., 1990) and were compared to the fruit and seed development in a control non transgenic plant (FIG. 8). The tomato fruits from several different transgenic plants which expressed the sps insert under the control of the Tob promoter did not develop seeds and in addition, displayed fruit tissue degeneration.

Figure 3C:
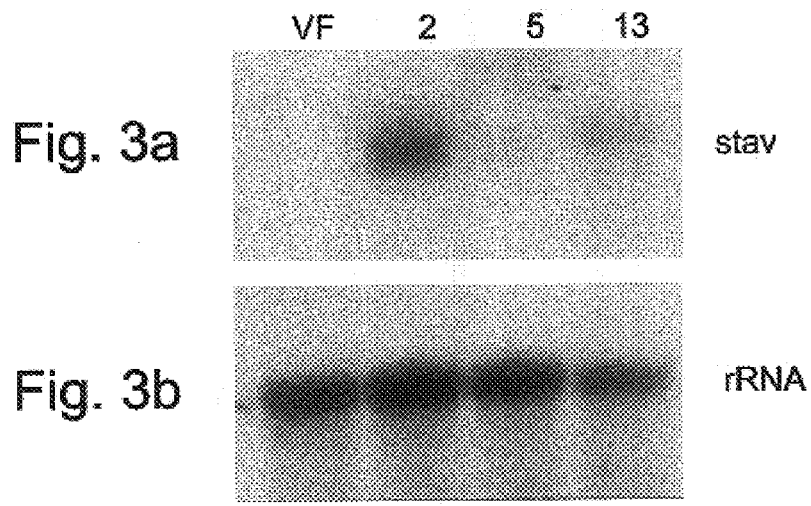
FIG. 3 demonstrates evaluation of streptavidin mRNA at steady state levels in transgenic plants transformed with the sps construct (FIG. 2) according to the present invention. Total RNA samples (10 µg) extracted from young leaves were subjected to Northern blot analysis using the sps streptavidin cassette (stav, panel A) and tomato rDNA fragment (panel B) as probes. The streptavidin mRNA level in each treatment was normalized relative to the rRNA content using the Phosphor-imager analytical program, and expressed in arbitrary units (panel C). VF-wild type strain.

Northern blot analysis was performed in order to correlate transgene expression level with the degree of symptoms observed. Total RNA was extracted from leaves of plants number 2, 5, 13 and the wild type VF strain. A radioactive $^{32}$P-sps fragment was used for probing (FIG. 3). Generally, the detection level was very low, as such, a long exposure time period (11 days, biomax film Kodak) of the film was needed. The highest hybridization signal was obtained for plant number 2 which showed strong and rapid degeneration (Table 4).

Germination Test of Seeds Derived from T0 Plants:

In order to determine the viability of seeds derived from T0 plants, a germination test was performed (Table 5). The germination rate of seeds derived from plant No. 2 was found to be 53% whereas the rate of the other transgenics was above 80%. The kanamycin sensitivity ratio was unexpectedly 0.4–0.7, instead of 0.25 in cases of normal segregation. All seedlings of plant No. 13 were kanamycin resistant, suggesting that the transgene cassette was integrated into its genome in more than one site.

Figure 4:
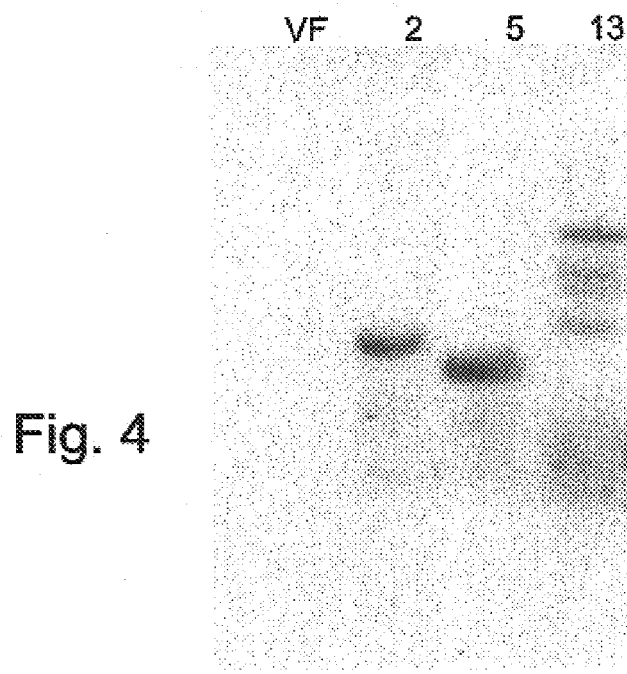
FIG. 4 demonstrates sps streptavidin cassette copy number in genome of transgenic plants by Southern blot analysis. DNA (10 µg) was digested with EcoRI and hybridized with a 780-bp PCR fragment of the nptII gene.

To confirm this result genomic Southern analysis was performed with DNA samples from plants 2, 5 and 13 and the wild type. Probing with $^{32}$P-labeled nptII-PCR fragment verified the existence of more than one copy of the streptavidin cassette in plant No. 13 and one copy in the other two transgenics (FIG. 4). In addition, it was shown that a daily application of biotin to T0 plants restored the germination to their otherwise non-germinating seeds (FIG. 6).

TABLE 5

Germination test of F1 plants

| Plant | No. Seeds | % Germination | No. KnR[a] | No. KnS[b] | % KnS[c] |
|---|---|---|---|---|---|
| 1 | 66 | 92 | 38 | 23 | 38 |
| 2 | 92 | 53 | 27 | 22 | 45 |
| 3 | 120 | 100 | 66 | 54 | 45 |
| 5 | 146 | 99 | 83 | 61 | 42 |
| 6 | 66 | 99 | 37 | 28 | 43 |
| 7 | 72 | 100 | 24 | 48 | 67 |
| 8 | 71 | 93 | 24 | 42 | 64 |
| 10 | 84 | 91 | 41 | 35 | 46 |
| 11 | 72 | 85 | 35 | 26 | 43 |
| 13 | 48 | 83 | 22 | 0 | — |

[a] number of kanamycin resistant seedlings.
[b] number of kanamycin sensitive seedlings.
[c] % kanamycin sensitive seedlings out of total seedlings obtained.

Morphology and Development of sps Transformed Plants:

The plants expressing the sps construct (FIG. 2) were evaluated for tissue degeneration level, as well as, development and morphology. The following degeneration symptoms were observed:

All the plants transfected with the sps construct were approximately 10–20% shorter than the control plants. The control plants were either transgenic plants transformed with the vector sequence or non-transgenic wild-type control plants. Moreover, all the plants transformed with the sps construct displayed similar branching patterns, having more stems per plant which resulted in a larger canopy as compared to both types of control plants.

About 30% of the plants which expressed the sps construct showed localized necrotic lesion(s) at different locations on the mature part of the plants' stem. The localized lesion increased in size (length and around in circumference) with time, resulting in stem collapse. The shoot tissue above this point desiccated and died.

Daily treatment of the sps construct transfected plants with a solution containing 2 μM biotin (by spraying), subsequent to the appearance of the initial necrotic lesion, stopped or prevented further development of degenerative symptoms. All of the plants treated with biotin remained green and vital throughout their development.

About 10% of the plants which expressed the sps construct did not flower at all and remained green throughout the growth cycle. These plants grew taller than the flowering plants.

About 25% of the plants which expressed the sps construct flowered but did not produce any fruits throughout their development.

About 40% of the plants which expressed the sps construct and developed fruit were seedless. Daily treatment of these plants, subsequent to appearance of the initial flower buds, with a solution containing 2 μM biotin (by spraying) resulted in the development of normal fruit and the restoration of normal seed development.

About 25% of the plants that expressed the sps construct developed normal fruit containing developed seeds, but these seeds did not germinate at all. Daily treatment of the plants resulted in the development of normal germinating seeds.

Some of the plants showed abnormal leaf development with severe growth retardation of leaflets. These symptoms were more prevalent in newly developed leaves which displayed chlorosis which lead to necrosis and death. Daily treatment of such plants subsequent to the appearance of the initial chlorotic symptoms on the young leaves, with a solution containing 2 μM biotin (by spraying) resulted in the development of normal leaves.

The strength of the binding affinity of streptavidin to biotin is the highest recorded between a protein and its ligand (Green 1975). Hence, its expression in the plant cell, in an active form, may decrease the cytosolic biotin pool and lead to inactivation of biotinylated proteins, culminating with plant tissue degeneration. Based on the results presented herein, it is believed that active biotin binding protein in sufficient amounts serves as a biotin sink regardless of its location and distribution within plant cells.

The toxic effect of streptavidin expression in a plant is dependent on a combination of several factors, which include, (i) the plant cytosolic biotin level, the bound vs. unbound ratio of biotin and it's compartmentalization within the cell, (ii) the expression level of streptavidin and its distribution, (iii) the accumulation level of streptavidin in the plant cell (RNA and protein turnover); (iv) the binding activity of the streptavidin towards biotin; and (v) the site of expression in the cell/plant. In the study presented here, several different streptavidin artificial genes were prepared in order to devise a streptavidin expression construct which yields the lowest toxicity to plant tissue while at the same time effect degeneration of somatic plat tissue. In addition, the toxicity level of this construct was selected such that reversal of the somatic cell degeneration could be effected by external application of biotin construct.

Figure 2:
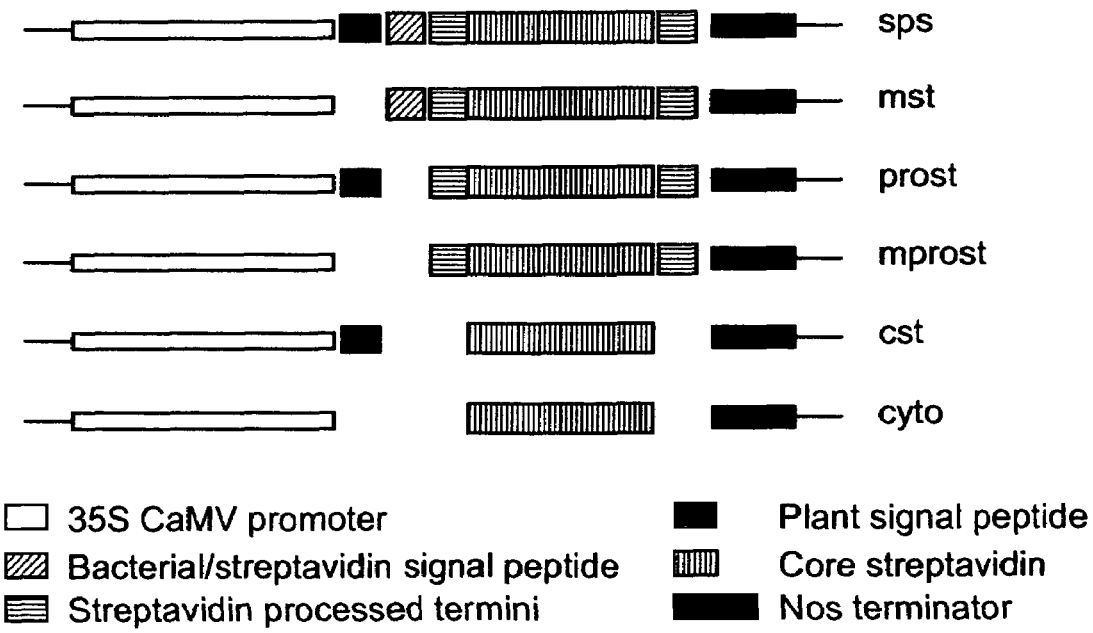
FIG. 2 is a schematic illustration of various streptavidin constructs utilized while reducing the present invention to practice.

Tomato, which according to the experiments described herein showed to contain a medial level of biotin compared to other crop plants tested, was chosen as a model plant. The toxicity of the various streptavidin artificial genes was first determined by transient expression assay in which, tomato seedlings were co-cultivated with Agrobacterium carrying these genes. The constructs were designed according to the structure of the bacterial protein. The bacterial streptavidin is first synthesized as a polypeptide containing signal peptide for secretion (Argarana et al., 1986), this form of streptavidin is represented in the "inst" insert (FIG. 2). This signal peptide is processed in the bacteria to yield a resulting streptavidin protein represented by the "mprost" insert (FIG. 2). Postsecretory modifications in the bacteria leads to the removal of amino acid residues from the N- and C-termini (Bayer et al., 198) and the minimal size for activity termed "core" streptavidin is generated, this core streptavidin is represented by the "cyto" insert.

In this study, six different constructs which embody the variant processed forms of streptavidin with ("sps", "prost" and "cst") or without ("mst", "mprost" and "cyto") the addition of a plant signal peptide for secretion in order to test whether trafficking of the artificial proteins out of the cell results in decreased toxicity, as opposed to the constructs with which localization of the streptavidin proteins in the cytosol is effected.

As the transient expression assay clearly demonstrates, the addition of plant signal peptide decreases the observed toxicity for each type of artificial streptavidin gene. The construct "sps" was found to provoke a weak tissue degeneration effect (see Table 3). This result may be as a direct result of the existence of two signal peptides, one derived from plants and the other bacterial which when co-expressed decrease the level of the accumulated protein due to incorrect processing leading to the destruction of this protein by cellular lysozomes. It can also be speculated that the streptavidin-preproprotein is not correctly folded and as a result biotin binding is reduced.

Although the "sps" construct was shown to be less toxic in transient expression assays, its toxicity to the whole plant should also be tested since the integration site of the transgene into the plant genome, and the number of copies integrated are crucial factors affecting its expression level. Therefore tomato plants were transformed with the "sps" construct, which effects degeneration of the somatic plant tissue but at the same time retains plant viability. Plantlets expressing this construct were examined at several developmental stages. Two thirds of the transformed plantlets died of severe degeneration of the young stems. These plants probably expressed the transgene in a level relatively higher than that of the other plantlets which survived and developed. During further development in the greenhouse 4 plants (transgenics 2, 3, 5 and 13) showed phenotype characteristic of stem degeneration at various severity levels. Spraying of biotin restored the degenerated tissue and enabled these plants to complete their life cycle. The other transgenic plants (1, 6, 7, 8, 10 and 11) appeared to have normal growth and development. However when seeds of all the transgenic plants were germinated under kanamycin selection, the segregation expected (3:1) was not obtained, suggesting that seeds development was most affected by the streptavidin expression. Seeds containing homozygous form of the transgene could not develop at all. Some of the seeds with the heterozygous forms were also affected, depending on the expression level of the streptavidin in the parent plant. They neither lost their viability (low germination rate) or didn't developed at all (kanamycin segregation ratio differ than 1:2).

The conclusions from streptavidin expression in whole plants are that (i) in addition to construction of artificially low expressing transgene, plants should be selected for individuals that express it at the lowest level, (ii) seeds development is very sensitive to streptavidin expression and can be used as a tool to identify low expressing plants (segregation ratio should be 1:3), although no alteration in plant growth could be observed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Alban, C., Baldet, P., Axiotis, S. and Douce, R. (1993) Purification and characterization of 3-methylcrotonyl-CoA carboxylase from higher plant mitochondria. Plant Physiol. 102: 957–965.
2. Alban, C., Baldet, P. and Douce, R. (1994). Localization and characterization of two structurally different forms of acetyl-CoA carboxylase in young pea leaves, of which one is sensitive to aryloxyphenoxypropionate herbicides. *Biochem. J.* 300: 557–565.
3. Andrews, S. C., Arosio, P., Bottke, W., Briat, J. F., von Darl, M., Harrison, P. M., Laulhere, J. P., Levi, S., Lobreaux, S. and Yewdall, S. J. (1992) Structure, function, and evolution of ferritins. J Inorg Biochem 47:161–74
4. Argarana C E, Kuntz I D, Birken S, Axel R, Cantor C R (1986) Molecular cloning and nucleic acid sequence of the streptavidin gene. *Nuc. Acids Res.* 14:1871–1882.
5. Baldet, P., Alban, C., Axiotis, S. and Douce, R. (1993a). Localization of free and bound biotin in cells from green pea leaves. Arch. Biochem. Biophys. 303:67–73.
6. Baldet, P., Alban, C., Axiotis, S., and Douce, R. (1992). Characterization of biotin and 3-methylcrotonyl-coenzyme A carboxylase in higher plant mitochondria. Plant Physiol 99: 450–455.
7. Baldet, P., Gerbling, H., Axiotis, S., Douce, R. (1993b). Biotin biosynthesis in higher plant cells: identification of intermediates. Eur. J. Biochem 217: 479–485.
8. Bayer. E. A., Ben-Hur, H., Hiller, Y. and Wilcheck, M. (1989) Postsecretory modifications of streptavidin. Biochem. J. 259:369–376.
9. Benfey P N and Chua N.-H. (1990). The cauliflower mosaic virus 35S promoter: combinational regulation of transcription in plants. Science 250:959–966.
10. Bradford M M (1976). Rapid and sensitive method for the quantification of microgram quantities of protein utilizing the principle of protein-dye binding. Anal. Biochem. 72:248–254.
11. Chee P P, Drong R P, Slighton J L: Using polymerase chain reaction to identify transgenic plants. In Gelvin S B, Schilperoorp R A (eds), Plant Molecular Biology Manual C3, pp. 1–28. Kluwer Academic Publishers, Belgium (1991).
12. Chen, Y., Wurtele, E S., Wang, X., Nikolau, B J (1993) Purification and characterization of 3-methylcrotonyl-CoA carboxylase from somatic embryos of *Daucus carola*. Arch. Biochem. Biophys. 303: 103–109.
13. Choi, J k., Yu, F., Wurtele, E S., Nikolau, B J (1995). Molecular cloning and characterization of the cDNA coding for the blotin-containing subunit of the chloroplastic acetyl-CoA carboxylase. Plant Physiol. 109: 619–625.
14. Cronan, J E (1989). The *E. coli* bio operon: transcriptional repression by an essential protein modification enzyme. Cell 58: 427–429.
15. Diez, T. A., Wurtele, E S., Nikolau, B J (1994) Purification and characterization of 3-methylcrotonyl-coenzyme A carboxylase from leaves of *Zea mays*. Arch. Biochem. Biophys. 310: 64–75.
16. Duval, M., DeRose, R., Job, C., Faucher, D., Douce, R. and Job, D. (1994). The major biotinyl protein from *Pisum sativum* seeds covalently binds biotin at a novel site. Plant Mol. Biol. 26:265–273.
17. Duval, M., Job, C., Alban, C., Douce, R. and Job, D. (1994b). Developmental patterns of free and protein-bound biotin during maturation and germination of seeds of *Pisum sativum*: characterization of a novel seed-specific biotinylated protein. Biochem. J. 299:141–150.
18. Ebel, J. and Halbrock K. (1977). Enzymes of flavone and flavonol glucosides biosynthesis. Coordinated and selective induction in cell-suspension cultures of *Petroselinum hortense*. Eur. J. Biochem. 75:201–209.
19. Ebel, J., Schmidt, W. E. and Loyal, R. (1984). Phytoalexin synthesis in soybean cells: elicitor induction of phenylalanine ammonia-lyase and chalcone synthase mRNAs and correlation with phytoalexin accumulation. Arch. Biochem. Biophys. 232:240–248.
20. Eizenberg, M. (1987). Biosynthesis of biotin and lipoic acid. In F C Neidhardt, J L Ingraham, K B Low, B. Magasani, M. Schaechter, H E Umbarger, eds, *Escherichia coli* and *Salmonella typhimurium*: Cellular and Molecular Biology. American Society for Microbiology, Washington, D.C., pp. 544–550.
21. Green N M. (1975) Avidin. Adv. Protein Chem. 29:85–133.
22. Harrison, P. M., Arthymiuk, P. J., Ford, G. C. Lawson, D. M., Smith, J, M, A, Treffry. A. and White J L, (1989) in Biomineralization: Chemical and Biochemical perspectives (Mann S, Webb J, and Williams R P J, eds) pp. 257–294, V C H, Weinheim.

23. Harwood, J. L. (1988) The site of action of some selective graminaceous herbicides is identified as acetyl-CoA carboxylase. Trends Biochem. Sci. 13:330–331.

24. Hood E E, Witcher D R, Maddock S, Meyer T, Baszczynski C, Bailey M, Flynn P, Register J, Marshall L, Bond D, Kulisek E, Kusnadi A, Evangelista R, Nikolov Z, Wooge C, Melligh R J, Hernan R, Kappel W K, Ritland D, Li C P, Howard J A (1997) Commercial production of avidin from transgenic maize: characterization of transformant, production, processing, extraction and purification. *Molec. Breeding* 3: 291–306.

25. Hood, E. E., Gelvin, S. B., Melchers, L. S., Hoekema, A. 1993. New *Agrobacterium* helper plasmids for gene transfer to plants. Transgenic Research 2:208–218

26. Knowles, J. R. (1989). The mechanism of biotin-dependent enzymes. Annu. Rev. Biochem. 58:195–221.

27. Kolattukudy, P. E., Croteau, R. and Buckner, J. S. (1976). Biochemistry of plant waxes. In Chemistry and Biochemistry of Natural Waxes. Edited by Kolattukudy, P. E. pp. 289–347. Elsevier Press, New York.

28. Kusnadi A. R., Hood E. E., Witcher D. R., Howard J. A. and Nikolov Z. L. (1998). Production and purification of two recombinant proteins from transgenic corn. Biotechnol Prog January–February; 14(1):149–55.

29. Lescure, A. M., Proudhon, D., Pesey, H., Ragland. M., Theil, E. C. and Briat, J.-F. (1991) Ferritin gene transcription is regulated by iron in soybean cell cultures. Proc Natl Acad Sci USA 88:8222–6.

30. Lessire, E. R., Bessoule. J.-J. and Cassagne, C. (1985) Solubilization of C18-CoA and C20-CoA elongases from *Allium porrum* L., epidermal cell microsomes. FEBS Lett. 187:314–320.

31. Lutcke. H. A., Chow, K. C., Mickel, F. S., Moss, K. A., Ken, H. F. and Scheele, G. A. (1987) Selection of AUG initiation codons differs in plants and animals. EMBO J. 6; 43–48.

32. Mozafar, A. (1993). Plant vitamins: agronomic, physiological, and nutritional aspects. CRC Press, London.

33. Nikolau, B. J., Wurtele, E. S. and Stumpf, P. K. (1984) Tissue distribution of acetyl-CoA carboxylase in leaves. Plant Physiol. 75:895–901.

34. Nikolau, B. J., Wurtele, E. S., Caffrey, J., Chen, Y., Crane, V., Diez, T., Huang, J.-Y., Mc Dowell, M. T., Shang, X.-M., Song, J., Wang, X. and Weaver, L. M. (1993). The biochemistry and moleclar biology of acetyl-CoA carboxylase and other biotin enzymes. In Biochemistry and Molecular Biology of Membrane and Storage Lipids in Plants. Edited by Murata, N. and Somerville, C. pp. 138–149. American Society of Plant Physiologists, Baltimore.

35. Ohlrogge, J. B., Kuhn, D. N. and Stumpf, P. K. (1979). Subcellular localization of acyl-carrier protein in leaf protoplasts of *Spinachina oleracea*. Proc. Natl. acad. Sci. USA 76:1194–1198.

36. Otsuka, A. J., Buoncristiani, M. B., Howard. P. K., Flamm, J., Johnson, C., Yamamoto, R., Uchida, K., Cook, C., Ruppert, J. and Matsuzaki, J. (1988) The *Escherichia coli* biotin biosynthetic enzyme sequences predicted from the nucleic acid sequence of the bio operon. J. Biol. Chem. 263:19577–19585.

37. Parker, W. B., Marshall, L. C. Burton, J. D., Somers, D. A., Wyse, D. L., Gronwald, J. W. and Gengenbach, B. G. (1990). Dominant mutations causing alterations in acetyl-CoA carboxylase confer tolerance to cyclohexanedione and aryloxyphenoxypropionate herbicides in maize. Proc. Natl. Acad. Sci. USA 87:7175–7179.

38. Patton, D. A., Johnson, M. and Ward, E. R. (1996a) Biotin synthase from *Arabidopsis thaliana*. cDNA isolation and characterization of gene expression. Plant Physiol. 112:371–378.

39. Patton, D. A., Volrath, S. and Ward, E. R. (1996b) Complementation of an *Arabidopsis thaliana* biotin auxotroph with an *Escherichia coli* biotin biosynthetic gene. Mol. Gen. Genet. 251:261–266.

40. Sambrook J, Fritsch E F, Maniatis T: Molecular Cloning, a Laboratory Manual, 2nd edition, Cold Spring Harbor Laboratory Press, NY (1989).

41. Schneider, T., Dinins, R., Robinson, Shelhammer, J., Meinke, D W. (1989). An embryo-lethal mutant of *Arabidopsis thaliana* is a biotin auxotroph. Dev. Biol. 131: 161–167.

42. Shelhammer, J., Meinke, D. (1990). Arrested embryos from the auxotroph of *Arabidopsis thaliana* contains reduced levels of biotin. Plant Physiol. 93: 1162–1167.

43. Shorrosh, B S., Dixon, R A., Ohlrogge, J B (1994). Molecular cloning characterization, and elicitation of acetyl-CoA carboxylase from alfalfa. Proc. Natl. Acad. Sci. USA 91: 4323–4327.

44. Song, J., Wurtele, E S., Nikolau, B J (1994). Molecular cloning and characterization of the cDNA coding for the biotin containing subunit of 3-methylcrotonyl-CoA carboxylase: identification of the biotin carboxylase and biotin-carrier domains. Proc. Natl. Acad. Sci USA 91: 5779–5783.

45. Theil, E. C. (1987) Ferritin: structure, gene regulation, and cellular function in animals, plants, and microorganisms. Annu Rev Biochem 56:289–315.

46. Tissot, G., Douce, R. and Alban, C. (1997). Evidence for multiple forms of biotin holocarboxylase synthase in pea (*Pisum sativum*) and in *Arabidopsis thaliana*: subcellular fractionation studies and isolation of a cDNA clone. Biochem. J. 323:179–188.

47. Van Engelen, F. A., Molthoff, J. w., Conner, A. J. and Nap, J. P. (1995) pBINPLUS—An improved plant transformation vector based on pBIN19. Transgenic Res. 4:288–290.

48. Van Wuytswinkle, O., Vansuyt, G., Grignon, N., Fourcroy, P. and Briat, J.-F. (1998) Iron homeostasis alteration in transgenic tobacco overexpressing ferritin. Plant J. 17:93–97

49. Watanabe K, Chikushi K, Adachi T, Shinizu M, Yoshida T, Mitsunaga T (1998) Thiamin-binding protein from sunflower seeds. J Nutr Sci Vitaminol 44:665–72.

50. Wang, X., Wurtele, E S, Nikolau, B J. (1995). Regulation of β-methyl-crotonyl-CoA carboxylase activity by biotinylation of the apoenzyme. Plant Physiol 108: 1133–1139.

51. Wurtele, E. S. and Nikolau, B. J. (1990). Plants contain multiple biotin enzymes: Discovery of 3-methylcrotonyl-CoA carboxylase, propionyl-CoA carboxylase and pyruvate carboxylase in the plant kingdom. Arch. Biochem. Biophys. 278:179–186.

52. Wurtele, E. S. and Nikolau, B. J. (1992) Differential accumulation of biotin enzymes during carrot somatic embryogenesis. Plant Physiol. 99:1699–1703.

53. Yamamoto, Y. T., Cheng, C L. and Conkling, M. A. (1990) Root-specific genes from tobacco and *Arabidopsis* homologous to an volutionarily conserved gene family of membrane channel proteins. Nucleic Acids Res 18:7449

54. Yanai, Y., Kawasaki, T., Shimada, H., Wurtele, E S., Nikolau, B J, Ichikawa, N. (1995). Genetic organizatioin of the 251-kDa acetyl-CoA carboxylase activity genes in *Arabidopsis*: tandem gene duplication has made two differentially expressed isozymes. Plant Cell Physiol. 36: 770–787.

What is claimed is:

1. A method of generating a plant having modified canopy size, wherein the method comprises:
   (a) transforming plants with a construct that expresses in cells of a young leaf and/or shoot tissue streptavidin operably linked to a signal peptide capable of self secretion, thereby depleting biotin in said cells of said young leaf and/or shoot tissue; and
   (b) selecting viable plants which exhibit degeneration of said young leaf and/or shoot tissue as compared to similar plants not expressing said streptavidin, thereby obtaining the plant having modified canopy size.

2. A method of generating a plant having seedless fruit, wherein the method comprises:
   (a) transforming plants with a construct that expresses streptavidin under the transcriptional control of a Tob promoter in cells of an embryonic tissue, said streptavidin operably linked to a signal peptide capable of self secretion, thereby depleting biotin in said cells of said embryonic tissue; and
   (b) selecting viable plants which exhibit degeneration of said embryonic tissue as compared to similar plants not expressing said streptavidin, thereby obtaining a plant having seedless fruit.

* * * * *

SEQUENCE LISTING

<160> NUMBER OF SEQ ID NOS: 24

<210> SEQ ID NO 1
<211> LENGTH: 563
<212> TYPE: DNA
<213> ORGANISM: Artificial sequence
<220> FEATURE:
<223> OTHER INFORMATION: 'sps'-streptavidin artificial gene

<400> SEQUENCE: 1

```
actgcagtta tgcgcaagat cgtcgttgca gccatcgccg tttccctgac cacggtctcg      60
attacggcca gcgcttcggc agacccctcc aaggactcga aggcccaggt ctcggccgcc     120
gaggccggca tcaccggcac ctggtacaac cagctcggct cgaccttcat cgtgaccgcg     180
ggcgccgacg gcgccctgac cggaacctac gagtcggccg tcggcaacgc cgagagccgc     240
tacgtcctga ccggtcgtta cgacagcgcc ccggccaccg acggcagcgg caccgccctc     300
ggttggacgg tggcctggaa gaataactac cgcaacgccc actccgcgac cacgtggagc     360
ggccagtacg tcgcggcgc cgaggcgagg atcaacaccc agtggctgct gacctccggc     420
accaccgagg ccaacgcctg gaagtccacg ctggtcggcc acgacaccct caccaaggtg     480
aagccgtccg ccgcctccat cgacgcggcg aagaaggccg gcgtcaacaa cggcaacccg     540
ctcgacgccg ttcagcagta gtc                                             563
```

<210> SEQ ID NO 2
<211> LENGTH: 186
<212> TYPE: PRT
<213> ORGANISM: Artificial sequence
<220> FEATURE:
<223> OTHER INFORMATION: 'sps'-streptavidin artificial gene product

<400> SEQUENCE: 2

```
Thr Ala Val Met Arg Lys Ile Val Val Ala Ala Ile Ala Val Ser Leu
1               5                   10                  15

Thr Thr Val Ser Ile Thr Ala Ser Ala Ser Ala Asp Pro Ser Lys Asp
            20                  25                  30

Ser Lys Ala Gln Val Ser Ala Ala Glu Ala Gly Ile Thr Gly Thr Trp
        35                  40                  45

Tyr Asn Gln Leu Gly Ser Thr Phe Ile Val Thr Ala Gly Ala Asp Gly
    50                  55                  60

Ala Leu Thr Gly Thr Tyr Glu Ser Ala Val Gly Asn Ala Glu Ser Arg
65                  70                  75                  80

Tyr Val Leu Thr Gly Arg Tyr Asp Ser Ala Pro Ala Thr Asp Gly Ser
                85                  90                  95

Gly Thr Ala Leu Gly Trp Thr Val Ala Trp Lys Asn Asn Tyr Arg Asn
            100                 105                 110

Ala His Ser Ala Thr Thr Trp Ser Gly Gln Tyr Val Gly Gly Ala Glu
        115                 120                 125

Ala Arg Ile Asn Thr Gln Trp Leu Leu Thr Ser Gly Thr Thr Glu Ala
    130                 135                 140

Asn Ala Trp Lys Ser Thr Leu Val Gly His Asp Thr Phe Thr Lys Val
145                 150                 155                 160

Lys Pro Ser Ala Ala Ser Ile Asp Ala Ala Lys Lys Ala Gly Val Asn
                165                 170                 175

Asn Gly Asn Pro Leu Asp Ala Val Gln Gln
            180                 185
```

```
<210> SEQ ID NO 3
<211> LENGTH: 564
<212> TYPE: DNA
<213> ORGANISM: Artificial sequence
<220> FEATURE:
<223> OTHER INFORMATION: 'mst'-streptavidin artificial gene

<400> SEQUENCE: 3
gtaaacaatg gctcgcaaga tcgtcgttgc agccatcgcc gtttccctga ccacggtctc    60
gattacggcc agcgcttcgg cagacccctc caaggactcg aaggcccagg tctcggccgc   120
cgaggccggc atcaccggca cctggtacaa ccagctcggc tcgaccttca tcgtgaccgc   180
gggcgccgac ggcgccctga ccggaaccta cgagtcggcc gtcggcaacg ccgagagccg   240
ctacgtcctg accggtcgtt acgacagcgc cccggccacc gacggcagcg gcaccgccct   300
cggttggacg gtggcctgga agaataacta ccgcaacgcc cactccgcga ccacgtggag   360
cggccagtac gtcggcggcg ccgaggcgag gatcaacacc cagtggctgc tgacctccgg   420
caccaccgag gccaacgcct ggaagtccac gctggtcggc cacgacacct tcaccaaggt   480
gaagccgtcc gccgcctcca tcgacgcggc gaagaaggcc ggcgtcaaca acggcaaccc   540
gctcgacgcc gttcagcagt agtc                                         564

<210> SEQ ID NO 4
<211> LENGTH: 184
<212> TYPE: PRT
<213> ORGANISM: Artificial sequence
<220> FEATURE:
<223> OTHER INFORMATION: 'mst'-streptavidin artificial gene product

<400> SEQUENCE: 4

Met Ala Arg Lys Ile Val Val Ala Ala Ile Ala Val Ser Leu Thr Thr
1               5                   10                  15

Val Ser Ile Thr Ala Ser Ala Ser Ala Asp Pro Ser Lys Asp Ser Lys
            20                  25                  30

Ala Gln Val Ser Ala Ala Glu Ala Gly Ile Thr Gly Thr Trp Tyr Asn
        35                  40                  45

Gln Leu Gly Ser Thr Phe Ile Val Thr Ala Gly Ala Asp Gly Ala Leu
    50                  55                  60

Thr Gly Thr Tyr Glu Ser Ala Val Gly Asn Ala Glu Ser Arg Tyr Val
65                  70                  75                  80

Leu Thr Gly Arg Tyr Asp Ser Ala Pro Ala Thr Asp Gly Ser Gly Thr
                85                  90                  95

Ala Leu Gly Trp Thr Val Ala Trp Lys Asn Asn Tyr Arg Asn Ala His
            100                 105                 110

Ser Ala Thr Thr Trp Ser Gly Gln Tyr Val Gly Gly Ala Glu Ala Arg
        115                 120                 125

Ile Asn Thr Gln Trp Leu Leu Thr Ser Gly Thr Thr Glu Ala Asn Ala
    130                 135                 140

Trp Lys Ser Thr Leu Val Gly His Asp Thr Phe Thr Lys Val Lys Pro
145                 150                 155                 160

Ser Ala Ala Ser Ile Asp Ala Ala Lys Lys Ala Gly Val Asn Asn Gly
                165                 170                 175

Asn Pro Leu Asp Ala Val Gln Gln
            180
```

<210> SEQ ID NO 5
<211> LENGTH: 492
<212> TYPE: DNA
<213> ORGANISM: Artificial sequence
<220> FEATURE:
<223> OTHER INFORMATION: 'prost'- streptavidin artificial gene

<400> SEQUENCE: 5

```
gactgcagtt gacccctcca aggactcgaa ggcccaggtc tcggccgccg aggccggcat    60
caccggcacc tggtacaacc agctcggctc gaccttcatc gtgaccgcgg gcgccgacgg   120
cgccctgacc ggaacctacg agtcggccgt cggcaacgcc gagagccgct acgtcctgac   180
cggtcgttac gacagcgccc cggccaccga cggcagcggc accgccctcg gttggacggt   240
ggcctggaag aataactacc gcaacgccca ctccgcgacc acgtggagcg gccagtacgt   300
cggcggcgcc gaggcgagga tcaacaccca gtggctgctg acctccggca ccaccgaggc   360
caacgcctgg aagtccacgc tggtcggcca cgacaccttc accaaggtga agccgtccgc   420
cgcctccatc gacgcggcga agaaggccgg cgtcaacaac ggcaacccgc tcgacgccgt   480
tcagcagtag tc                                                       492
```

<210> SEQ ID NO 6
<211> LENGTH: 162
<212> TYPE: PRT
<213> ORGANISM: Artificial sequence
<220> FEATURE:
<223> OTHER INFORMATION: 'prost'- streptavidin artificial gene product

<400> SEQUENCE: 6

```
Thr Ala Val Asp Pro Ser Lys Asp Ser Lys Ala Gln Val Ser Ala Ala
1               5                   10                  15

Glu Ala Gly Ile Thr Gly Thr Trp Tyr Asn Gln Leu Gly Ser Thr Phe
            20                  25                  30

Ile Val Thr Ala Gly Ala Asp Gly Ala Leu Thr Gly Thr Tyr Glu Ser
        35                  40                  45

Ala Val Gly Asn Ala Glu Ser Arg Tyr Val Leu Thr Gly Arg Tyr Asp
    50                  55                  60

Ser Ala Pro Ala Thr Asp Gly Ser Gly Thr Ala Leu Gly Trp Thr Val
65                  70                  75                  80

Ala Trp Lys Asn Asn Tyr Arg Asn Ala His Ser Ala Thr Thr Trp Ser
                85                  90                  95

Gly Gln Tyr Val Gly Gly Ala Glu Ala Arg Ile Asn Thr Gln Trp Leu
            100                 105                 110

Leu Thr Ser Gly Thr Thr Glu Ala Asn Ala Trp Lys Ser Thr Leu Val
        115                 120                 125

Gly His Asp Thr Phe Thr Lys Val Lys Pro Ser Ala Ala Ser Ile Asp
    130                 135                 140

Ala Ala Lys Lys Ala Gly Val Asn Asn Gly Asn Pro Leu Asp Ala Val
145                 150                 155                 160

Gln Gln
```

<210> SEQ ID NO 7
<211> LENGTH: 495
<212> TYPE: DNA
<213> ORGANISM: Artificial sequence
<220> FEATURE:
<223> OTHER INFORMATION: 'mprost'- streptavidin artificial gene

<400> SEQUENCE: 7

```
gtaaacaatg gctgacccct ccaaggactc gaaggcccag gtctcggccg ccgaggccgg    60
catcaccggc acctggtaca accagctcgg ctcgaccttc atcgtgaccg cgggcgccga   120
cggcgccctg accggaacct acgagtcggc cgtcggcaac gccgagagcc gctacgtcct   180
gaccggtcgt tacgacagcg ccccggccac cgacggcagc ggcaccgccc tcggttggac   240
ggtggcctgg aagaataact accgcaacgc ccactccgcg accacgtgga gcggccagta   300
cgtcggcggc gccgaggcga ggatcaacac ccagtggctg ctgacctccg gcaccaccga   360
ggccaacgcc tggaagtcca cgctggtcgg ccacgacacc ttcaccaagg tgaagccgtc   420
cgccgcctcc atcgacgcgg cgaagaaggc cggcgtcaac aacggcaacc cgctcgacgc   480
cgttcagcag tagtc                                                   495
```

<210> SEQ ID NO 8
<211> LENGTH: 161
<212> TYPE: PRT
<213> ORGANISM: Artificial sequence
<220> FEATURE:
<223> OTHER INFORMATION: 'mprost'- streptavidin artificial gene product

<400> SEQUENCE: 8

```
Met Ala Asp Pro Ser Lys Asp Ser Lys Ala Gln Val Ser Ala Ala Glu
1               5                   10                  15

Ala Gly Ile Thr Gly Thr Trp Tyr Asn Gln Leu Gly Ser Thr Phe Ile
            20                  25                  30

Val Thr Ala Gly Ala Asp Gly Ala Leu Thr Gly Thr Tyr Glu Ser Ala
        35                  40                  45

Val Gly Asn Ala Glu Ser Arg Tyr Val Leu Thr Gly Arg Tyr Asp Ser
    50                  55                  60

Ala Pro Ala Thr Asp Gly Ser Gly Thr Ala Leu Gly Trp Thr Val Ala
65                  70                  75                  80

Trp Lys Asn Asn Tyr Arg Asn Ala His Ser Ala Thr Thr Trp Ser Gly
                85                  90                  95

Gln Tyr Val Gly Gly Ala Glu Ala Arg Ile Asn Thr Gln Trp Leu Leu
            100                 105                 110

Thr Ser Gly Thr Thr Glu Ala Asn Ala Trp Lys Ser Thr Leu Val Gly
        115                 120                 125

His Asp Thr Phe Thr Lys Val Lys Pro Ser Ala Ala Ser Ile Asp Ala
    130                 135                 140

Ala Lys Lys Ala Gly Val Asn Asn Gly Asn Pro Leu Asp Ala Val Gln
145                 150                 155                 160

Gln
```

<210> SEQ ID NO 9
<211> LENGTH: 369
<212> TYPE: DNA
<213> ORGANISM: Artificial sequence
<220> FEATURE:
<223> OTHER INFORMATION: 'cst'- streptavidin artificial gene

<400> SEQUENCE: 9

```
actgcaggca tcaccggcac ctggtacaac cagctcggct cgaccttcat cgtgaccgcg    60
ggcgccgacg gcgccctgac cggaacctac gagtcggccg tcggcaacgc cgagagccgc   120
tacgtcctga ccggtcgtta cgacagcgcc cggccaccg acggcagcgg caccgccctc   180
ggttggacgg tggcctggaa gaataactac cgcaacgccc actccgcgac cacgtggagc   240
```

```
ggccagtacg tcggcggcgc cgaggcgagg atcaacaccc agtggctgct gacctccggc      300
accaccgagg ccaacgcctg gaagtccacg ctggtcggcc acgacacctt caccaaggtg      360
aagccgtag                                                              369
```

<210> SEQ ID NO 10
<211> LENGTH: 122
<212> TYPE: PRT
<213> ORGANISM: Artificial sequence
<220> FEATURE:
<223> OTHER INFORMATION: 'cst'- streptavidin artificial gene product

<400> SEQUENCE: 10

```
Thr Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
                20                  25                  30

Ala Val Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro
        115                 120
```

<210> SEQ ID NO 11
<211> LENGTH: 376
<212> TYPE: DNA
<213> ORGANISM: Artificial sequence
<220> FEATURE:
<223> OTHER INFORMATION: 'cyto' - streptavidin artificial gene

<400> SEQUENCE: 11

```
gtaaacaatg gctggcatca ccggcacctg gtacaaccag ctcggctcga ccttcatcgt       60
gaccgcgggc gccgacggcg ccctgaccgg aacctacgag tcggccgtcg gcaacgccga      120
gagccgctac gtcctgaccg gtcgttacga cagcgccccg gccaccgacg gcagcggcac      180
cgccctcggt tggacggtgg cctggaagaa taactaccgc aacgcccact ccgcgaccac      240
gtggagcggc cagtacgtcg gcggcgccga ggcgaggatc aacacccagt ggctgctgac      300
ctccggcacc accgaggcca acgcctggaa gtccacgctg gtcggccacg acaccttcac      360
caaggtgaag ccgtag                                                      376
```

<210> SEQ ID NO 12
<211> LENGTH: 122
<212> TYPE: PRT
<213> ORGANISM: Artificial sequence
<220> FEATURE:
<223> OTHER INFORMATION: 'cyto' - streptavidin artificial gene product

<400> SEQUENCE: 12

```
Met Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
                20                  25                  30
```

```
Ala Val Gly Asn Ala Glu Ser Arg Tyr Val Leu Thr Gly Arg Tyr Asp
         35                  40                  45

Ser Ala Pro Ala Thr Asp Gly Ser Gly Thr Ala Leu Gly Trp Thr Val
     50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ala Asn Ala Trp Lys Ser Thr Leu Val
                100                 105                 110

Gly His Asp Thr Phe Thr Lys Val Lys Pro
            115                 120
```

```
<210> SEQ ID NO 13
<211> LENGTH: 63
<212> TYPE: DNA
<213> ORGANISM: Triticum aestivum

<400> SEQUENCE: 13
atgaagacct ttctcatcct tgtcctcctt gctattgtgg cgaccaccgc cacaactgca    60
gtt                                                                 63

<210> SEQ ID NO 14
<211> LENGTH: 20
<212> TYPE: PRT
<213> ORGANISM: Triticum aestivum

<400> SEQUENCE: 14

Met Lys Thr Phe Leu Ile Leu Val Leu Leu Ala Ile Val Ala Thr Thr
 1               5                  10                  15

Ala Thr Thr Ala
             20

<210> SEQ ID NO 15
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 15
actgcagtta tgcgcaagat cgtcg                                         25

<210> SEQ ID NO 16
<211> LENGTH: 18
<212> TYPE: DNA
<213> ORGANISM: Artificial sequence
<220> FEATURE:
<223> OTHER INFORMATION: synthetic oligonucleotide

<400> SEQUENCE: 16
gactactgct gaacggcg                                                 18

<210> SEQ ID NO 17
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 17
gtaaacaatg gctcgcaaga tcgtcgttgc ag                                 32
```

```
<210> SEQ ID NO 18
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 18
gactgcagtt gacccctcca aggactcgaa ggcccag                    37

<210> SEQ ID NO 19
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 19
gtaaacaatg gctgacccct ccaaggactc gaaggcccag                 40

<210> SEQ ID NO 20
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 20
actgcaggca tcaccggcac ctggtacaac                            30

<210> SEQ ID NO 21
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 21
ctacggcttc accttggtga ag                                    22

<210> SEQ ID NO 22
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 22
gtaaacaatg gctggcatca ccggcacctg gtacaac                    37

<210> SEQ ID NO 23
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 23
cacgcaggtt ctccggccgc                                       20

<210> SEQ ID NO 24
<211> LENGTH: 20
<212> TYPE: DNA
<213> ORGANISM: Artificial sequence
<220> FEATURE:
<223> OTHER INFORMATION: synthetic oligonucleotide
```

-continued

```
<400> SEQUENCE: 24
tgcgctgcga atcgggagcg                                               20
```